(12) United States Patent
Tryggvason et al.

(10) Patent No.: US 7,105,291 B2
(45) Date of Patent: Sep. 12, 2006

(54) NEPHRIN GENE AND PROTEIN

(75) Inventors: Karl Tryggvason, Djursholm (SE); Marjo Kestila, Oulu (FI); Ulla Lenkkeri, Oulu (FI); Minna Mannikko, Philadelphia, PA (US)

(73) Assignee: Biostratum, Inc., Durham, NC (US)

( * ) Notice: Subject to any disclaimer, the term of this patent is extended or adjusted under 35 U.S.C. 154(b) by 0 days.

(21) Appl. No.: 09/759,622

(22) Filed: Jan. 12, 2001

(65) Prior Publication Data

US 2002/0004589 A1 Jan. 10, 2002

Related U.S. Application Data

(62) Division of application No. 09/040,774, filed on Mar. 18, 1998, now Pat. No. 6,207,811.

(51) Int. Cl.
*C12Q 1/68* (2006.01)
*C12P 19/34* (2006.01)

(52) U.S. Cl. .................. 435/6; 435/91.2; 536/23.1
(58) Field of Classification Search ............. 435/7.1, 435/6; 530/287.1, 350; 536/23.1
See application file for complete search history.

(56) References Cited

OTHER PUBLICATIONS

Enger, R. "Nephrin, the pressor hormone of the Kidney", Arch. exptl. Path. Pharmakol. (1947) 204:217-27.*
Altschul, S.F., Gish, W., Miller, W., Myers, E.W., and Lipman, D.J. (1990) Basic local alignment search tool. J. Mol. Biol. 215, 403-10.
Appel, R.D. Bairoch, A. And Hochstrasser, D.F. (1994) A new generation of information retrieval tools for biologists: the example of the ExPASy WWW server. Trends Biochem. Sci. 19: 258-260.
Barker, D. Hostikka, S.L., Zhou, J., Chow, L.T., Oliphant, A.R., Gerken, S.C., Gregory, M.C., Skolnick, M.H., Atkin, C.L. and Tryggvason, K. (1990) Identification of Mutations in the COL4A5 collagen gene in Alport Syndrome. Science 248, 1224-1227.
Brümmendott, T., and Rathjen, F.G. (1994) Cell adhesion molecules 1: Immunoglobulin superfamily. Protein profile 1, 951-1058.
Burge, C. And Karlin, S. (1997) Prediction of complete gene structures in human genomic DNA. J. Mol. Biol. 168, 78-94.
Chapelle, A. de la (1993) Disease gene mapping in isolated human populations: the example of Finland. J. Med. Genet. 30: 857-865.
Dolan, M., Horchar, T., Rigatti, B., and Hassell, J.R. (1997) Identification of sites in domain I perlecan that regulate heparan sulfate synthesis, J. Biol. Chem. 272, 4316-4322.
Fahrig, T., Landa, C., Psheva, P., Kühn, K., and Schacher, M. (1987) Characterization of binding properties of the myelin-associated glycoprotein to extracellular matrix constituents. EMBO J. 6, 2875-2883.
Fuchshuber, A., Niaudet, P., Gribouval, O., Genevieve, J., Gubler, M-C., Broyer, M. And Antignac, C. (1996) Congenital Nephrotic Syndrome of the Finnish type: linkage to the locus in a non-Finnish population. Pediatr. Nephrol. 10: 135-138.
Hästbacka, J., Chapelle, A. de la, Mahtani, M.M., Clines, G., Reebe-Daly, M.P., Daly, M., Hamilton, B.A., Kusumi, K., Trivedi, B., Weacer, A., Coloma, A., Lovett, M., Buckler, A., Kaitila, I., and Lander, E.S. (1994) The Diastrophic dysplasia gene encodes a novel sulfate transporter: positional cloning by fine-structure linkage disequilibrium mapping. Cell 78, 1073-1087.
Hillier et al. (1997) "WashU-NCI human EST project", Genbank Locus AA678622.
Holmberg, C., Antikainene, M., Rönnholm, K., Ala-Houhala, M. And Jalanko, H. (1995) Management of congenital nephrotic syndrome of the Finnish type, Pediatr. Nephrol. 9: 87-93.
Ikonen, E., Baumann, M., Grön, K., Syvänen, A-C., Enomaa, N., Halila, R., Aula, P. And Peltonen, L., (1991) Aspartylglucosaminuria: cDNA encoding human aspartylglucosaminidase and the missense mutation causing the disease. EMBO J. 10: 51-58.
Jurka, J., Klonowski, P., Dagman, V., Pelton, P. (1996) CENSOR—a program for identification and elimination of repetitive elements from DNA sequences. Computers and Chemistry vol. 20 (No. 1): 119-122.
Kallunki, P., and Tryggvason, K. (1992) Human basement membrane heparan sulfate proteoglycan core protein: a 467 kD protein containing multiple domain resmbling elements of the low density lipoprotein receptor, laminin, neural cell adhesion molecules, and epidermal growth factor. J. Cell Biol. 116, 559-571.
Kasinath, B.S. and Kanwar, Y.S. (1993) Glomerular basement membrane: biology and physiology. In: Molecular and cellular aspects of basement membranes (D. Rorhbach and R. Timpl. eds), Academic Press, pp. 89-106.
Kawai, S. Nomura, S., Harano, T., Fukushima, T., & Osawa, G. (1996) The COL4A5 gene in Japanese Alport syndrome patients: spectrum of mutations of all exons. Kidney Int. 49, 814-822.
Keino-Masu, K., Masu. M., Hinck, L., Leonardo, E.D., Chan, S.S.Y., Culotti, J.G., and Tessier-Lavigne, M. (1996) Cell 87, 175-185.
Kestila, M., et al. "Positionally cloned Gene for a novel Glomerular Protein (Nephrin) is Mutated in Congenital Nephrotic Syndrome," Molecular Cell, vol. 1, No. 4, Mar. 1998, pp. 575-582.
Kestilä, M., Männikkö, M., Holmberg. C., Korpela, K., Savolainen, E.R., Peltonen, L. and Tryggvason, K. (1994a) Exclusion of eight genes as mutated loci in congenital nephrotic syndrome of the Finnish type. Kidney Int. 45, 986-990.
Kestilä, M., Männikkö, M., Holmberg, C., Gyapay, G. Weissenbach, J. Savolainen, E.R., Peltonen, L. and Tryggvason K. (1994b) Congenital nephrotic syndrome of the Finnish type maps to the long arm of chromosome 19. Am. J. Hum. Genet. 54, 757-764.
Knebelmann, B. Breillat, C., Forestier, L., Arrondel, C., Jacassier, D., et al. (1996) Spectrum of mutations in the COL4A5 collagen gene in X-linked Alport syndrome, Am. J., Hum. Genet. 59, 1221-1232.

(Continued)

*Primary Examiner*—Jeffrey Fredman
(74) *Attorney, Agent, or Firm*—Hamilton, Brook, Smith & Reynolds, P.C.

(57) ABSTRACT

The present invention provides for compositions and methods for detecting susceptibility for basement membrane disease, in particular Congenital nephrotic syndromes of the Finnish type. The present invention provides for nucleic acids and protein for use in methods and compositions for the diagnosis of disease and identification of small molecule therapeutics for treatment of such disease, in particular of proteinuria associated with kidney disease.

27 Claims, 7 Drawing Sheets

OTHER PUBLICATIONS

Koskimies, O. (1990) Genetics of congenital and early infantile nephrotic syndromes. In: Spitzer, A., Avner, E.D. (Eds) Inheritance of kidney and uritary tract diseases. Kluwer, Boston, Dordrecht and London, p. 131-138.

Laine, J.,Jalanko, H.,Holthöfer, H. Krogerus, L., Rapola, J., von Willebrand, E., Lautenschlager, I., Salmela, K. and Holmberg, C. (1993) Post-transplantation nephrosis in congenital nephrotic syndrome of the Finnish-type. Kidney Int. 44: 867-874.

Lamerden, J.E., et al. "Sequence Analysis of a 1Mb Region in 19q13.1," EMBL Sequence Database, Jul. 11, 1997.

Lenkkeri, U., et al, "Structure of the Gene for Congenital Nephrotic Syndrome of the Finnish Type (NPHS1) and Characterization of Mutations," American Journal of Human Genetics, vol. 64, No. 1, Jan. 1999, pp. 51-56.

Ljungberg, P., Jalanko, H., Holmberg, C., and Holthöfer, H. (1993) Congenital nephrosis of the Finnish type (CNF): Matrix components of the glomerular basement membranes and of cultured mesangial cells. Histochem J. 25: 606-612.

Mahan, J.D., Mauer, S.M. Sibley R.K. and Vernier, R.L. (1984) Congenital nephrotic syndrome: Evolution of medical management and results of renal transplantation. J. Pediatr. 105: 549-557.

Männikkö, M., Kestilä, M., Holmberg, C. Norio, R., Ryynänen, M., Olsen, A., Peltonen, L. And Tryggvason, K. (1995) Fine mapping and haplotype analysis of the locus for congenital nephrotic syndrome on chromosome 19q13.1. Am J. Hum. Genet. 57: 1377-1383.

Männikkö, M., Kestilä, M., Lenkkeri, U., Alakurtti, H., Holmberg, C., Leisti, J., Salonen, R., Aula, P., Mustonen, A., Peltonen, L., and Tryggvason, K., (1997) Improved prenatal diagnosis of the congenital nephrotic syndrome of the Finnish type name based on DNA analysis, Kidney Int. 51: 868-872.

Noonan, D.M., Fulle, A., Valente, P., Cai, S., Horigan, E., Sasaki, M., Yamada, Y., and Hassell, J.R. (1991) The complete sequence of perlecan, a basement membrane heparan sulfate proteoglycan, reveals extensive similarity with laminin A chain, low density lipoprotein receptor, and the neural cell adhesion molecule. J. Biol. Chem. 266, 22939-22947.

Olsen, A. Georgescu, A., Johnson, S. and Carrano, A.V. (1996) Assembly of a 1-Mb restriction-mapped cosmid contig spanning the candidate region for Finnish congenital nephrosis (NPHS1) in 19q13.1. Genomics 34: 223-225.

Pesheva, P., Gennarini, G., Goridis, C., and Schacher, M. (1993) The F3/11 cell adhesion molecule mediates the repulsion of neurons by the extracellular matrix glycoprotein J1-160/180. Neuron 10, 69-82.

Rapola, J. Huttunen, N.P. and Hallman, N. (1992) Congenital and infantile nephrotic syndrome. In: Edelman CM (ed.) Pediatric Kidney Disease. 2nd ed. Little, Brown and Company, Boston. vol. 2: 1291-1305.

Renieri, A., Bruttini, M., Galli, L., Zanelli, P., Neri, T., et al. (1996) X-linked Alport syndrome: an SSCP based mutation survey over all 51 exons of the COL4A5 gene. Am. J. Hum. Genet. 58, 1192-1204.

Solovyev, V.V., Salamov, A.A., Lawrence, C.B. (1994) Predicting internal exons by oligonucleotide composition and discriminant analysis of spliceable open reading frames. Nucl. Acids Res. 22(24): 5156-5163.

Stratagene Catalog. (1988) p. 39.

Tryggvason, K. (1996) Mutations in type IV collagen genes in Alport syndrome. In: Molecular pathology and Genetics of Alport syndrome (ed. K. Tryggvason). Contrib. Nephrol., 117, 154-171, Karger, Basel Tryggvason, K. and Kovalainen, K. (1975) Number of nephrons in normal human kidneys and kidneys of patients with the congenital nephrotic syndrome. Nephron 15: 62-68.

Tryggvason, K. Kovelainen, K. (1975) Number of nephrons in normal human kidneys and kidneys of patients with the congenital nephrotic syndrome. Nephron 15: 62-68.

Uberbacher, E.C. and Mural, R.J. (1991) Locating protein-coding regions in human DNA sequences by a multiple sensor-neural network approach, Proc. Natl. Acad. Sci. USA 88: 11261-11265.

Zisch, A.H., D'allessandri, L., Ranscht, B., Falchetto, R. Winterhalter, K.H., and Vaughan, L. (1992) Neuronal cell adhesion molecule contactin/F11 binds to tenascin via its immunoglobulin-like domains. J. Cell Biol. 119, 203-213.

\* cited by examiner

```
   1  MALGTTLRAS LLLLGLLTEG L↓AQLAIPASV PRGFWALPEN LTVVEGASVE
  51  LRCGVSTPGS AVQWAKDGLL LGPDPRIPGF PRYRLEGDPA RGEFHLHIEA
 101  CDLSDDAEYE CQVGRSEMGP ELVSPRVILS ILVPPKLLLL TPEAGTMVTW
 151  VAGQEYVVNC VSGDAKPAPD ITILLSGQTI SDISANVNEG SQQKLFTVEA
 201  TARVTPRSSD NRQLLVCEAS SPALEAPIKA SFTVNVLFPP GPPVIEWPGL
 251  DEGHVRAGQS LELPCVARGG NPLATLQWLK NGQPVSTAWG TEHTQAVARS
 301  VLVMTVRPED HGAQLSCEAH NSVSAGTQEH GITLQVTFPP SAIIILGSAS
 351  QTENKNVTLS CVSKSSRPRV LLRWWLGWRQ LLPMEETVMD GLHGGHISMS
 401  NLTFLARRED NGLTLTCEAF SEAFTKETFK KSLILNVKYP AQKLWIEGPP
 451  EGQKLRAGTR VRLVCLAIGG NPEPSLMWYK DSRTVTESRL PQESRRVHLG
 501  SVEKSGSTFS RELVLVTGPS DNQAKFTCKA GQLSASTQLA VQFPPTNVTI
 551  LANASALREG DALNLTCVSV SSNPPVNLSW DKEGERLEGV AAPPRRAPFK
 601  GSAAARSVLL QVSSRDHGQR VTCRAHSAEL RETVSSFYRL NVLYRPEFLG
 651  EQVLVVTAVE QGEALLPVSV SANPAPEAFN HTFRGYRLSP AGGPRHRILS
 701  SGALHLWNVT RADDGLYQLH CQNSEGTAEA RLRLDVHYAP TIRALQDPTE
 751  VNVGGSVDIV CTVDANPILP GMFNWERLGE DEEDQSLDDM EKISRGPTGR
 801  LRIHHAKLAQ AGAYQCIVDN GVAPPARRLL RLVVRFAPQV EHPTPLTKVA
 851  AAGDSTSSAT LHCRARGVPN IVFTWTKNGV PLDLQDPRYT EHTYHQGGVH
 901  SSLLTIANVS AAQDYALFTC TATNALGSDQ TNIQLVSISR PDPPSGLKVV
 951  SLTPHSVGLE WKPGFDGGLP QRFCIRYEAL GTPGFHYVDV VPPQATTFTL
1001  TGLQPSTRYR VWLLASNALG DSGLPDKGTQ LPITTPGLHQ PSGEPEDQLP
1051  TEPPSGPSGL PLLPVLFALG GLLLLSNASC VGGVLWQRRL RRLAEGISEK
1101  TEAGSEEDRV RNEYEESQWT GERDTQSSTV STTEAEPYYR SLRDFSPQLP
1151  PTQEEVSYSR GFTGEDEDMA FPGHLYDEVE RTYPPSGAWG PLYDEVQMGP
1201  WDLHWPEDTY QDPRGIYDQV AGDLDTLEPD SLPFELRGHL V
```

FIG. 4A

NEPHRIN GENE AND PROTEIN

This is a divisional of application Ser. No. 09/040,774, filed Mar. 18, 1999 now U.S. Pat. No. 6,207,811.

BACKGROUND OF THE INVENTION

Congenital nephrotic syndrome of the Finnish type (CNF, NPHS1, MIM 256300) is an autosomal recessive disorder, and a distinct entity among congenital nephrotic syndromes. It is characterized by massive proteinuria at the fetal stage and nephrosis at birth. Importantly, NPHS1 appears to solely affect the kidney and, therefore, it provides a unique model for studies on the glomerular filtration barrier.

The primary barrier for ultrafiltration of plasma in renal glomeruli comprises three layers; a fenestrated endothelium, a 300–350 nm thick glomerular basement membrane (GBM), and slit pores, i.e. diaphragms located between the foot processes of the epithelial cells. This barrier is a highly sophisticated size-selective molecular sieve whose molecular mechanisms of function are still largely unclarified. It is anticipated that the GBM, a tightly cross-linked meshwork of type IV collagen, laminin, nidogen and proteoglycans, contains pores that restrict the penetration of large proteins and cells, and, additionally, it has been hypothesized that anionic heparan sulfate proteoglycan components contribute to an electric barrier for macromolecules (Kasinath and Kanwar, 1993). The glomerular filter is affected in a large number of acquired and inherited diseases resulting in extensive leakage of plasma albumin and larger proteins leading to nephrotic syndrome and end stage renal disease. Understanding of the molecular mechanisms of the glomerular filtration process and its pathology is of fundamental importance for clinical medicine, which, in turn, may facilitate novel developments for diagnosis and treatment of complications in primary and secondary diseases of the kidney. Genetic diseases with defects in the filtration barrier as major symptoms can serve as models for providing such knowledge.

Congenital nephrotic syndromes (NPHS) form a heterogenous group of diseases characterized by massive proteinuria at or shortly after birth (Rapola et al., 1992). Nephrotic syndrome can be primary, acquired, or a part of other syndromes. Congenital nephrotic syndrome of the Finnish type (CNF, NPHS1) is a distinct entity among NPHS. It is an autosomal recessive disorder with an incidence of 1:10,000 births in Finland, but considerably less in other countries (Norio, 1966; Huttunen, 1976). The disease manifests itself already at the fetal stage with heavy proteinuria in utero, demonstrating early lesions of the glomerular filtration barrier. The pathogenesis of NPHS1 has remained obscure. There are no pathognomonic pathologic features, the most typical histological finding of NPHS1 kidneys being dilation of the proximal tubuli (Huttunen et al. 1980). The kidneys are also large and have been found to contain a higher amount of nephrons than age-matched controls (Tryggvason and Kouvalainen, 1975). Electron microscopy reveals no abnormal features of the GBM itself, although there is a loss of foot processes of the glomerular epithelial cells, a finding characteristic for nephrotic syndromes of any cause. Analyses of GBM proteins, such as type IV collagen, laminin, and heparan sulfate proteoglycan have not revealed abnormal findings in NPHS1 (e.g. see Ljungberg et al. 1993, Kestilä et al. 1994a). NPHS1 is a progressive disease, usually leading to death during the first two years of life, the only life-saving treatment being kidney transplantation (Holmberg et al. 1995). Importantly, most transplanted patients have, thus far, not developed extrarenal complications, suggesting that the mutated gene product is highly specific for kidney development and/or glomerular filtration function. However, about 20% of the patients have developed post-transplantation nephrosis the cause of which is unknown (Laine et al., 1993; Holmberg et al., 1995).

Due to its high specificity for the glomerular filtration process, NPHS1 provides a unique model disease for studies on this important kidney function. Since there was no strong candidate gene for the disease, we have used the positional cloning approach in our attempts to identify the CNF gene, and have localised the gene to a 150 kb region on chromosome 19q13.1 (Kestilä et al., 1994b; Männikkö et al., 1995). We have identified a novel critical region and shown it to be mutated in NPHS1. The gene product is a novel transmembrane protein, which in the human embryo shows a high expression level in renal glomeruli.

SUMMARY OF THE INVENTION

The present invention provides for the novel protein Nephrin and the gene encoding for this protein. The present invention encompasses a novel DNA nucleic acid sequence which is the nucleic acid sequence of SEQ ID NO:1 which encodes for the nephrin protein. The present invention also encompasses the protein encoded for by the coding regions of the nucleic acid sequence of SEQ ID NO:1 which has the amino acid sequence of SEQ ID NO:2. In particular, the present invention also encompasses the mature nephrin protein in which the signal peptide has been cleaved off.

The present invention encompasses method, reagents and kits for screening individuals for the presence of mutated Nephrin gene for diagnosis, pre-natal screening, or post-natal screening for susceptibility to glomerular nephrosis or basement membrane disease. In particular, the present invention provides for screening for congenital nephrotic syndromes of the Finnish type (NPHS1).

The present invention provides for methods, reagents and kits for the therapeutic treatment of basement membrane disease associated with defective endogenous Nephrin gene product. Thus the present invention provides for therapeutic treatment using Nephrin protein, and in particular using protein produced by recombinant DNA methods. In addition, the present invention provides for gene therapy using therapeutic nucleic acid constructs containing the Nephrin gene, or substantially similar DNA sequence thereto.

BRIEF DESCRIPTION OF THE DRAWINGS

FIG. 1A, is a physical map of the 920 kb region between markers D19S208 and D19S224. FIG. 1B, is a diagram of overlapping cosmid clones spanning the 150 kb critical region containing the NPHS1 gene. Location of polymorphic markers are indicated by arrows. FIG. 1C, is a diagram showing the location of five genes, NPHS1, APLP1, A, B, C, characterised and searched for mutations in this study.

FIG. 1D, is a drawing showing a schematic structure of the NPHS1 gene;

FIG. 2 shows a northern blot analysis of nephrin expression (the NPHS1 gene product) with mRNA from human embryonic and adult tissues. The northern filters containing 2 ug of human poly(A) RNA from four fetal and eight adult tissues (Clontech) were hybridized with a 1,371 bp nephrin cDNA probe (exons 1–10) made by RT-PCR from fetal kidney poly(A) RNA.

FIG. 4 is a diagram of the Nucleotide-derived amino acid sequence of nephrin (the NPHS1 gene product) and predicted domain structure. FIG. 4A (SEQ ID NO: 2), is the predicted N-terminal signal sequence is 22 residues, the cleavage site being marked with an arrow. A putative transmembrane domain (spanning residues 1,059–1,086) is shown in bold and underlined. The putative extracellular part of the protein contains eight Ig-like modules (boxed), and one fibronectin type III—like module adjacent to the transmembrane domain (boxed with a bold line, residues 941–1025). Cysteine residues are indicated by black dots and the ten putative N-glycosylation sites in the extracellular part of the protein are underlined. FIG. 5 shows the results of expression of nephrin mRNA in human embryonic kidney by in situ hybridization.

DETAILED DESCRIPTION OF THE INVENTION

Figure 1:
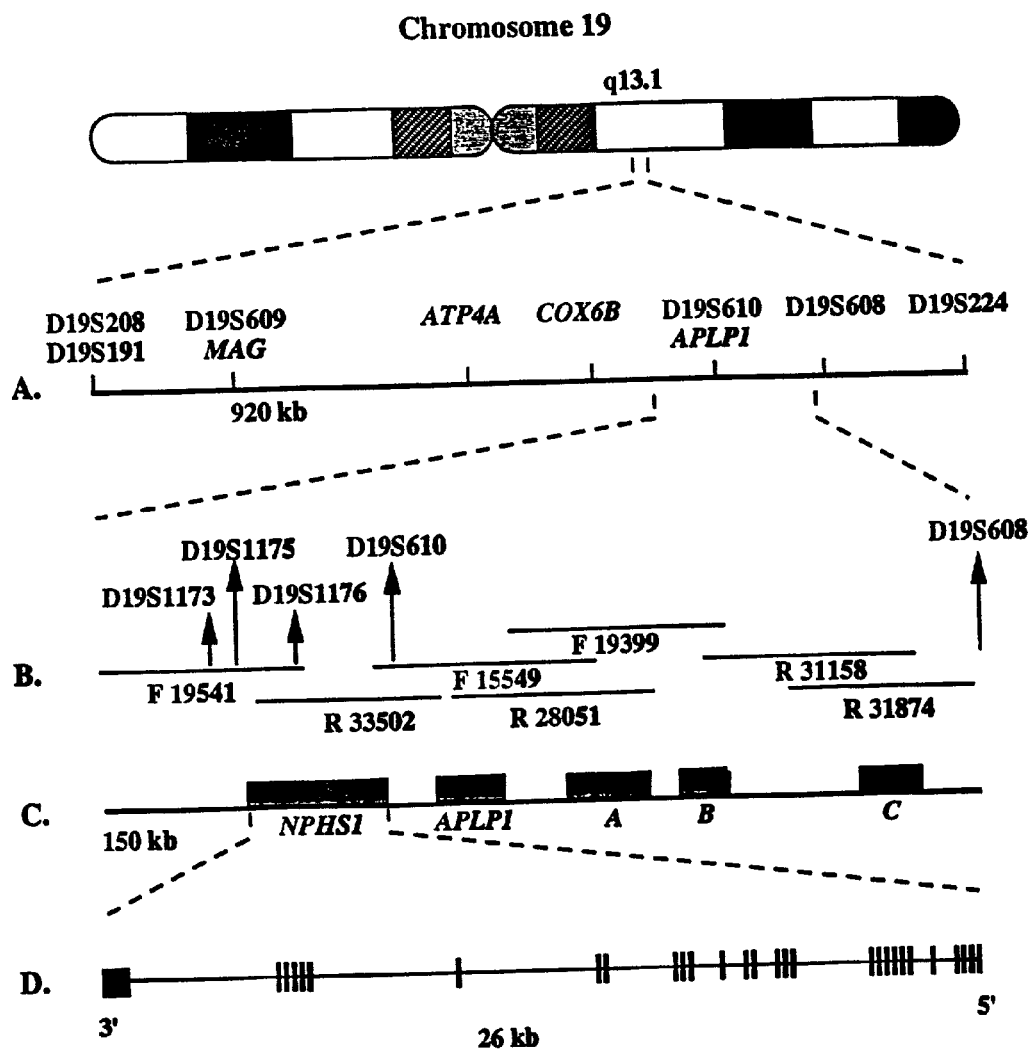
FIG. 1 is a drawing showing a physical map of the NPHS1 locus at 19q13.1 and genomic organization of the NPHS1 gene.

Congenital nephrotic syndrome of the Finnish type (CNF, NPHS1, MIM 256300) is an autosomal recessive disorder, and a distinct entity among congenital nephrotic syndromes. It is characterized by massive proteinuria at the fetal stage and nephrosis at birth. Importantly, NPHS1 appears to solely affect the kidney and, therefore, it provides a unique model for studies on the glomerular filtration barrier. The NPHS1 gene has been localized to 19q13.1, and in the present study linkage disequilibrium was used to narrow the critical region to 150 kilobases which were sequenced. At least 10 novel genes, and one encoding amyloid precursor like protein were identified in this region. Five of the genes, all of which showed some expression in kidney, were analyzed by sequencing all their 63 exons in NPHS1 patients. Two mutations, a 2-bp deletion in exon 2 and a single base change in exon 26, both leading to premature stop codons were found in a novel 29-exon gene. The mutations were found either as homozygous or compound heterozygous in 44 out of 49 patients, 4 patients having the 2 bp deletion in one allele, the other potential mutation still being unknown. None among controls was found homozygous or compound heterozygous for the mutations. The gene product, termed nephrin, is a 1,241-residue putative transmembrane protein of the immunoglobulin family of cell adhesion molecules which by northern and in situ hybridization was shown to be kidney glomerulus-specific. The results demonstrate a crucial role for nephrin in the development or function of the kidney filtration barrier.

The invention will be more clearly understood by examination of the following examples, which are meant by way of illustration and not limitation.

EXAMPLE 1

Methods and Procedures

Sequencing of Cosmid Clones

Isolation of cosmid clones spanning the region between D19S208 and D19S608 has been reported previously (Olsen et al., 1996). DNA of cosmid clones F19541, R33502, F15549, R28051, F19399, R31158 and R31874 was mechanically sheared by nebulization and fragments of 1000–2000 bp were isolated and subcloned into M13 phage, prior to random sequencing using ABI 377 automated DNA sequencers.

Analysis of Sequence

In order to develop new microsatellite markers, repeat regions were searched from the sequence, and three of them (D19S1173, D19S1175, D19S1176) were found to be polymorphic. Homology comparisons were performed using BLASTX and BLASTN programs (Altschul et al., 1990). Prior to BLASTN analyses, the nucleotide sequence was filtered using CENSOR (Jurka et al., 1996) to mask out repeat regions like Alu sequences. Exon prediction was made using GRAIL II (Uberbacher and Mural, 1991), GENSCAN (Burge and Karlin, 1997), FGENEH and HEXON (Solovyeh et al., 1994) programs, and prediction of the protein structure was made using BLASTP (Altschul et al., 1990) and EXPASY molecular biology server (Appel et al., 1994). The mutation search was performed by comparing patient sequences to the normal genomic sequence using the FASTA program of the GCG package (Genetics Computer Group, 1996).

Isolation of cDNAs cDNAs were generated by PCR from poly(A) RNA from different tissues using primers based on the exon sequences. The PCR fragments were sequenced and used for screening of cDNA libraries. Marathon ready cDNA kits (Clontech Laboratories) were also used to characterize the 5' and 3' extremities of the cDNAs. Comparison of the cDNA and genomic sequences were made to establish the sizes of introns, as were intron sequences at acceptor and donor splice sites.

Southern and Northern Blots and in Situ Hybridization Analyses

For Southern analyses samples containing 10 μg of genomic DNA were digested with different restriction enzymes and electrophreses on 1% agarose gels, transferred to nylon membranes and hybridized with the cDNA probe. In multiple-tissue northern analysis poly(A) RNAs from 8 adult and 4 fetal tissues were studied (Clontech). Hybridization was done in ExpressHyb buffer at 65° C. using a cDNA clone containing exons 1–10.

For in situ hybridization a fragment from the NPHS1 cDNA clone (corresponding to exon 10) was labeled with digoxigenin (Boehringer Mannheim), cut to about 150 base pair fragments by alkaline hydrolysis, and then used as a probe. Tissue sections of 7 μm from a 23-week human embryonic kidney were treated with 0.2M HCl, 0.1M triethanolamine buffer, pH 8.0, containing 0.25% (v/v) acetic anhydride and 100 μg/ml proteinase K. The sections were hybridized with the probe at 62° C. for 16 h. After rinsing in 50% formamide and standard sodium citrate, the probe was immunologically detected with an antibody to digoxigenin conjugated to alkaline phosphate enzyme (Boehringer Mannheim). The color was developed with NBT and BCIP.

Mutation Analysis

In this study we analyzed 49 Finnish NPHS1 patients, their parents and a total of 54 healthy siblings. The diagnosis of NPHS1 is based on severe proteinuria, a large placenta (>25% of birth weight), nephrotic syndrome during the first weeks of life, and exclusion of other types of congenital nephrotic syndrome (Koskimies 1990). Additionally, samples from 83 control individuals were analysed.

The NPHS1 gene was analysed by PCR-amplifying and sequencing all exon regions from genomic DNA. The sequences of the primers for exon 2 were 5'GAGAAAGCCAGACAGACGCAG3' (5' UTR) (SEQ ID NO: 3) and 5'AGCTTCCGCTGGTGGCT3' (intron 2) (SEQ ID NO: 4), and the sequences of the primers for exon 26 were 5'CTCGGGGAGACCCACCC3' (intron 23) (SEQ ID NO: 5) and 5'CCTGATGCTAACGGCAGGGC3' (intron 26) (SEQ ID NO: 6). PCR reactions were performed in a total volume of 25 ul, containing 20 ng of template DNA, 1× AmpliTaq buffer (Perkin-Elmer), 0.2 mM of each nucleotide, 50 ng of primers and 0.5 U AmpliTaq Gold DNA polymerase. The reactions were carried out for 30 cycles with denaturation at 95° C. for 1 min, annealing at 60° C. for 1 min, and extension at 72° C. for 1 min. In the first cycle denaturation was carried out for 12 min, and extension in the last cycle was for 8 min. PCR products were separated by 1.5% agarose gel, sliced off and purified by the QiaexII system (Qiagen). The purified PCR product was sequenced using specific primers employing dRhodamine dye-terminator chemistry and an ABI377 automated sequencer (Perkin-Elmer).

When screening for the NPHS1 Fin-major mutation from parents, siblings and controls, a 100 bp PCR product containing the exon 2 deletion site was amplified using a radioactively end-labeled primer, and electrophoresed on 6% polyacrylamide gels. The second NPHS1 Fin-minor mutation could be screened for using a novel restriction site for DdeI. The 140 bp amplified PCR product was digested with DdeI and the products (140 bp or 90 bp+50 bp) were separated on an agarose gel (1% SeaKem agarose-3% NuSieve agarose).

In general, methods and procedures for performing molecular biological and biochemical techniques are known in the art and can be found in available texts and references, such as for example Sambrook et al., (1989) *Molecular Cloning: a laboratory manual*, $2^{nd}$ edition (Cold Spring Harbor Laboratory Press, Cold Spring Harbor, N.Y.); *Short Protocols in Molecular Biology*, $2^{nd}$ edition (edited by Ausubel et al., John Wiley & Sons, New York, 1992); Davis et al., (1986) *Basic Methods in Molecular Biology* (Elsevier, New York); *Gene Expression Technology* (edited by David Goeddel, Academic Press, San Diego, Calif., 1991).

EXAMPLE 2

Characterization of Genes at the CNF Locus

Following localisation of the NPHS1 gene to 19q13.1, overlapping cosmid clones from the interval of interest between markers D19S208 and D19S224 were isolated (Männikkö et al. 1995; Olsen et al., 1996). Based on the significant linkage disequilibrium observed with D19S608 and D19S610, as well as the new microsatellite markers, D19S1173, D19S1175, and D19S1176, identified in this study, the NPHS1 gene was fine-mapped between D19S1175 and D19S608, in close vicinity of D19S1176 and D19S610 (FIG. 1). Southern hybridization analyses of NPHS1 patient DNA with genomic clones did not reveal variations, suggesting that the NPHS1 mutations do not represent major genomic rearrangements. The 150 kb critical region was sequenced in its entirety, and the sequence was searched for potential candidate genes using exon prediction programs and data base similarity searches. Based on those analyses, the critical region was estimated to include over 100 potential exons. Similarity searches revealed one previously known gene, i.e. APLP1 encoding an amyloid precursor-like protein (Lenkkeri et al., in press) and eight distinct expressed sequence tags (ESTs). Together the analyses indicated the presence of at least ten novel genes in the critical region.

FIG. 1 illustrates a physical map of the NPHS1 locus at 19q13.1 and genomic organisation of the NPHS1 gene. FIG. 1A, Physical map of the 920 kb region between D19S208 and D19S224. FIG. 1B, Overlapping cosmid clones spanning the 150 kb critical region containing the NPHS1 gene. Location of polymorphic markers are indicated by arrows. FIG. 1C, Location of five genes, NPHS1, APLP1, A, B, C, characterised and searched for mutations in this study. FIG. 1D, Schematic structure of the NPHS1 gene.

Using Grail and Genscan exon prediction programs and sequences from cDNAs, the exon/intron structures of five of the genes, NPHS1 (FIG. 1), APLP1, A, B, and C (not shown) were determined. Although steady state transcript levels varied, northern analyses revealed expression of all the genes in kidney, and with the exception of NPHS1, also in other tissues. Therefore, none of them could be excluded as the NPHS1 gene and all were subjected to mutation analysis.

EXAMPLE 3

Identification of the NPHS1 Gene

Haplotype analyses of NPHS1 chromosomes have revealed two major classes in Finnish patients (Männikkö et al., 1995; this study). The first one containing haplotypes 1-1-1-6-g-2-8-9 and 1-1-1-6-g-6-4-2 (markers D19S1173, D19S1175, D19S1176, D19S610, RFLP of gene B, D19S608, D19S224, D19S220, respectively) is the most common one found in 78% of Finnish NPHS1 chromosomes. The second haplotype class, 3-5-3-6-a-8-10-x, is found in 13% of cases. The remaining 9% of observed haplotypes show totally different allele combinations, and have been thought to represent other mutations. Two major haplotype classes could represent the same mutation, because they both share allele 6 of D19S610. However, the present results demonstrated that they represent two different mutations.

Since Southern hybridization analyses did not reveal any major gene rearrangements, mutations were searched by direct sequencing of PCR-amplified exon regions of, if necessary, all the genes of this region.

The 17 exon APLP1 gene located distal to D19S610 did not show variations between patients and controls, and was excluded as the NPHS1 gene (Lenkkeri et al., in press). Also, the novel genes A, B and C, containing 9, 5 and 3 exons, respectively, did not have sequence variants segregating with NPHS1, and could similarly be excluded as the NPHS1 genes (data not shown). A fourth novel gene (NPHS1) located proximal to D19S610 encoding a transcript of about 4.3 kb was shown to be strongly expressed in human embryonic and adult kidneys, no clear signals above background being observed in other tissues (FIG. 2).

Figure 2A:
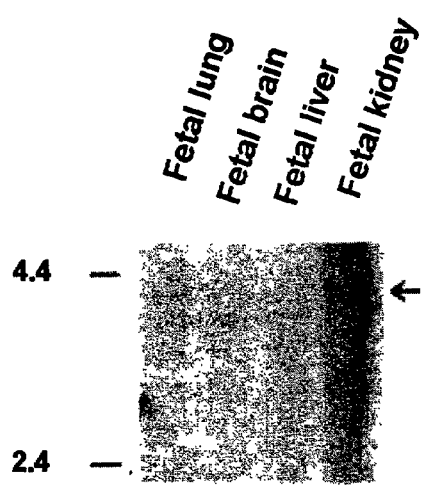
FIG. 2A, shows distinct expression can be seen only with fetal kidney RNA (arrow).
Figure 2B:
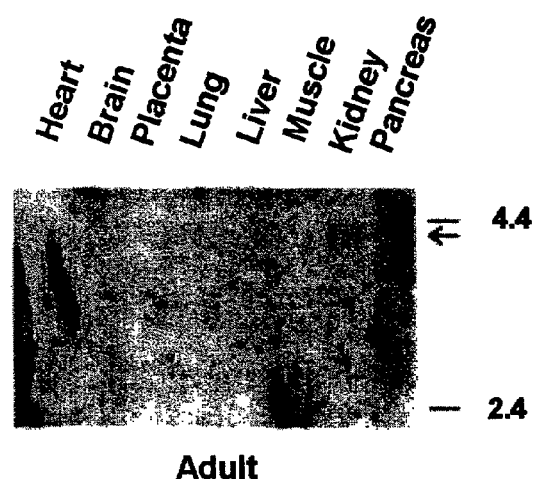
FIG. 2B, shows results using RNA from adult tissues, intense signal is only observed in a 4.3 kb band with kidney RNA (arrow), the other tissues exhibiting only insignificant if any positive signals. The tissues studied are marked above the filter and molecular size markers (kb) are shown to the sides of the filters.

FIG. 2 illustrates the results of Northern analysis of nephrin expression with mRNA from human embryonic and adult tissues. The northern filters containing 2 ug of human poly(A) RNA from four fetal and eight adult tissues (Clontech) were hybridized with a 1,371 bp nephrin cDNA probe (exons 1–10) made by RT-PCR from fetal kidney poly(A) RNA. In FIG. 2A, Distinct expression can be seen only with fetal kidney RNA (arrow). In FIG. 2B, Using RNA from adult tissues, intense signal is only observed in a 4.3 kb band with kidney RNA (arrow), the other tissues exhibiting only insignificant if any positive signals. The tissues studied are marked above the filter and molecular size markers (kb) are shown to the sides of the filters.

Therefore, this gene was a strong candidate for NPHS1. Full-length cDNA for the transcript was constructed using fetal kidney poly(A) mRNA (Clontech) and PCR primers made based on the predicted exon structure. The gene was found to have a size of 26 kb and to contain 29 exons (FIG. 1).

Figure 3:
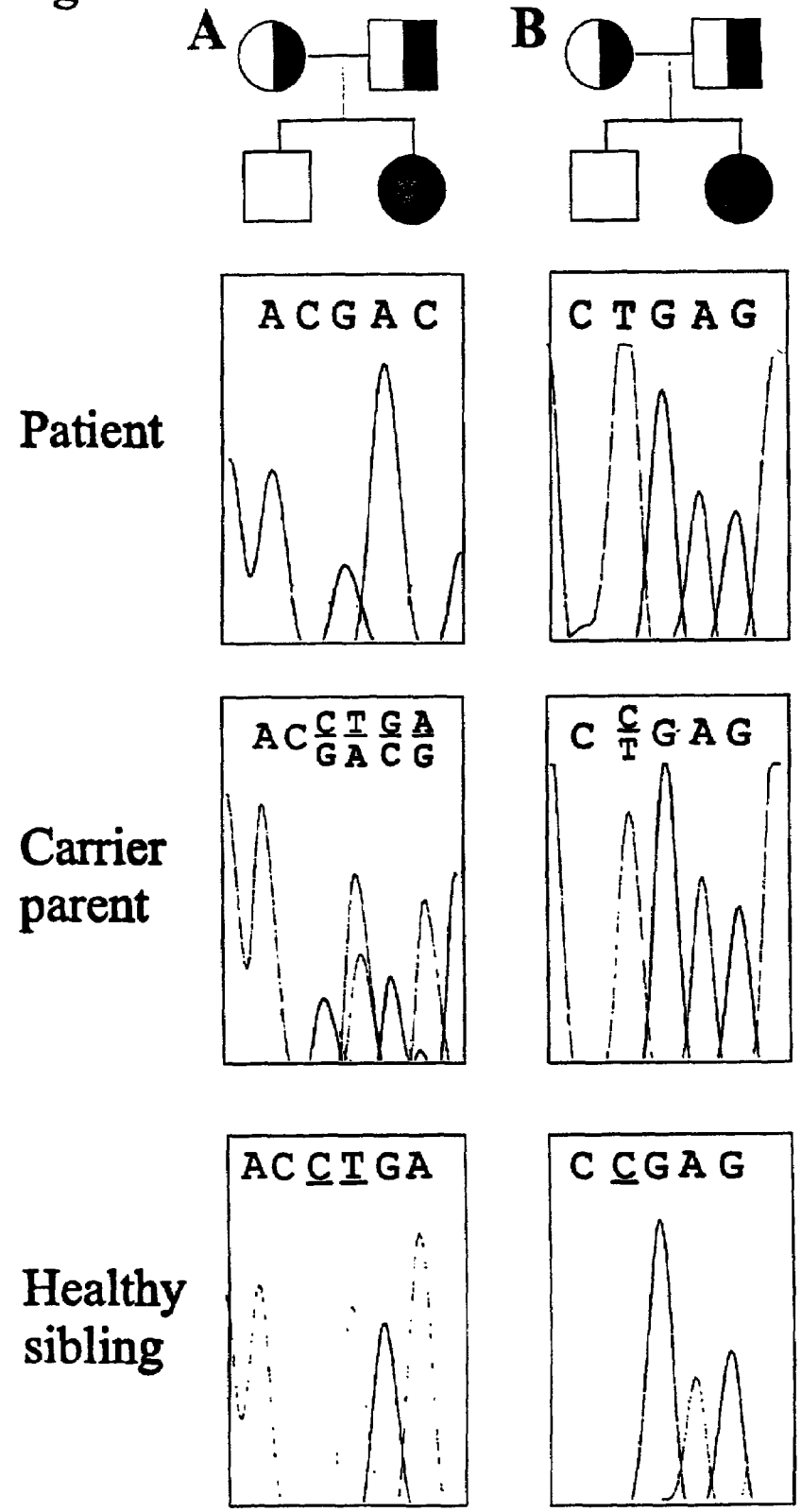
FIG. 3 is a diagram of Mutation analysis of the NPHS1 gene. Left: (A) Pedigree of an NPHS1 family with an affected child having a 2-bp deletion in exon 2. Sequences of the deletion point shown from patient (homozygous), parent (heterozygous) and a healthy sibling. Right: (B) Pedigree of an NPHS1 family with an affected child having a nonsense mutation in exon 26. Sequences of the mutated region are shown from patient (homozygous), parent (heterozygous) and a healthy sibling.

Exon sequencing analyses revealed the presence of two major mutations in over 90% of NPHS1 chromosomes (FIG. 3). FIG. 3 illustrates mutation analysis of the NPHS1 gene. Left: (A) Pedigree of a NPHS1 family with an affected child having a 2-bp deletion in exon 2. Sequences of the deletion point shown from patient (homozygous), parent (heterozygous) and a healthy sibling. Right: (B) Pedigree of a NPHS1 family with an affected child having a nonsense mutation in exon 26. Sequences of the mutated region are shown from patient (homozygous), parent (heterozygous) and a healthy sibling.

The first mutation, a 2-bp deletion in exon 2 causes a frameshift resulting in the generation of a stop codon within the same exon. This mutation was found in all NPHS1 chromosomes with the haplotype 1-1-1-6-g-2-8-9 and 1-1-1-6-g-6-4-2 (total of 76 chromosomes). One out of 83 control individuals was heterozygous for the Fin-major mutation. The second sequence variant found in the NPHS1 gene was a nonsense mutation CGA→TGA in exon 26, present in patients with haplotype 3-5-3-6-a-8-10-x (13 chromosomes), and three patients with different haplotypes. None of the parents, healthy siblings, or controls (total of 230 individuals) were homozygous or compound heterozygous for the two mutations identified here. Since the gene cloned in this study is the one involved in a hereditary nephrotic syndrome, we refer to it as NPHS1 gene.

Out of 49 NPHS1 patients studied, 32 were homozygous for the 2-bp deletion in exon 2 (Fin-major), four were homozygous for the nonsense mutation in exon 26 (Fin-minor), and eight were compound heterozygotes. Four patients had the Fin-major mutation in one allele, the other potential mutation still being unknown. One patient had neither one of the two mutations.

EXAMPLE 4

Characterization of the NPHS1 Gene Product

The cDNA-predicted amino acid sequence of the NPHS1 protein (nephrin) is 1,241 residues (FIG. 4), with a calculated molecular mass of 134,742 without posttranslational modifications.

Figure 4B:
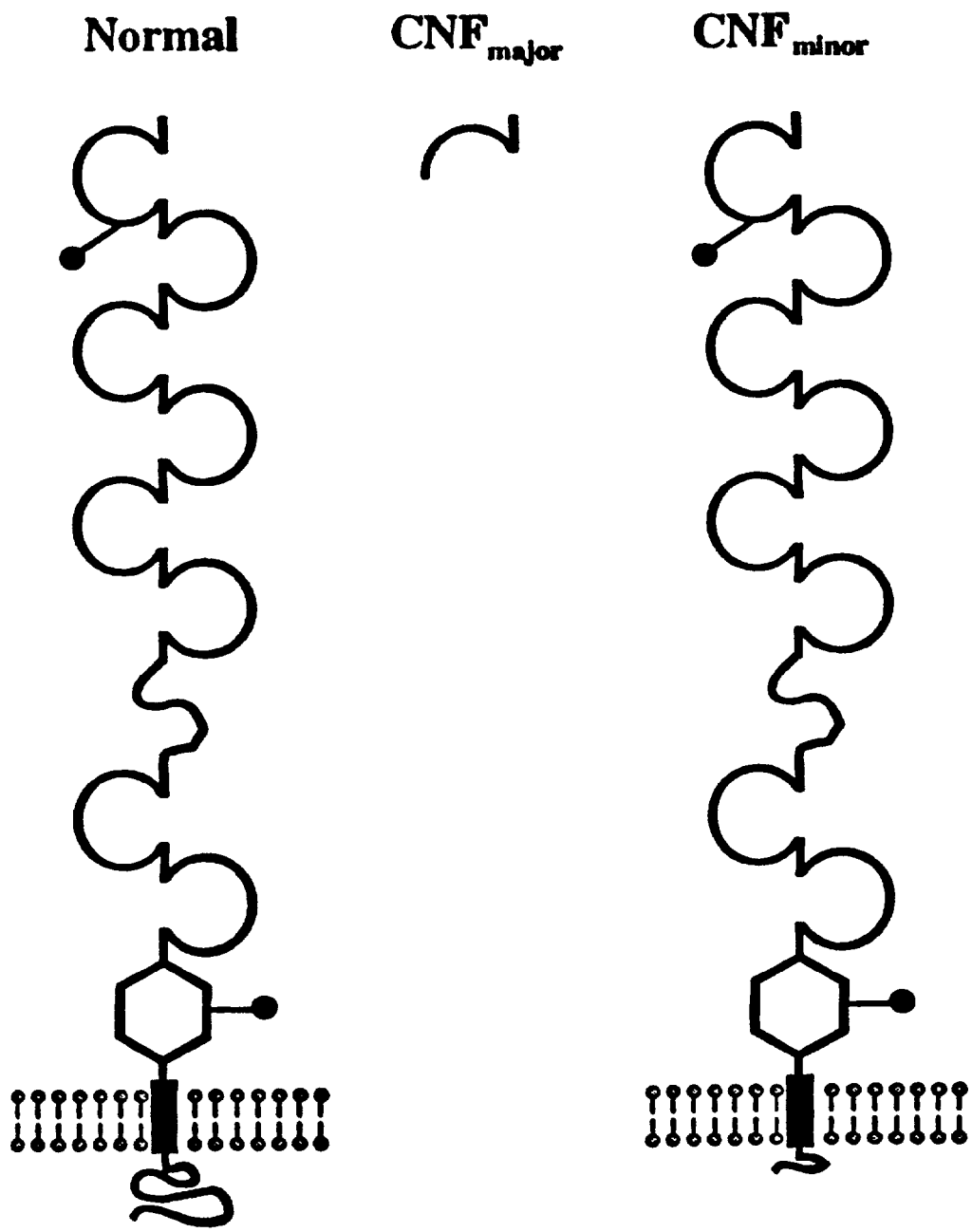
FIG. 4B shows the predicted domain structure of normal nephrin and the predicted effects of the two mutations (Fin-major and Fin-minor) identified in this study. The Ig-like modules are depicted by partial circles and the fibronectin type III like-motif by a hexagon. The transmembrane domain is shown as a black rectangle located in a membrane lipid bilayer. The locations of two free cysteine residues are indicated by lines with a black dot at the end. The Fin-major mutation would result in the production of part of the signal peptide and a short nonsense sequence. The Fin-minor mutation would result in a nephrin molecule lacking a part of the cytosolic domain.

FIG. 4 shows Nucleotide-derived amino acid sequence of nephrin and predicted domain structure (the NPHS1 gene product). FIG. 4A illustrates the predicted N-terminal signal sequence is 22 residues, the cleavage site being marked with an arrow. A putative transmembrane domain (residues 1,059–1086) is shown in bold and underlined. The putative extracellular part of the protein contains eight Ig-like modules (boxed), and one fibronectin type III-like module adjacent to the transmembrane domain (boxed with a bold line). Cysteine residues are indicated by black dots and the ten putative N-glycosylation sites in the extracellular part of the protein are underlined. FIG. 4B illustrates predicted domain structure of normal nephrin (the NPHS1 gene product) and the predicted effects of the two mutations (Fin-major and Fin-minor) identified in this study. The Ig-like modules are depicted by partial circles and the fibronectin type III like-motif by a hexagon. The transmembrane domain is shown as a black rectangle located in a membrane lipid bilayer. The locations of three free cysteine residues are indicated by lines with a black dot at the end. The major NPHS1 mutation would result in the production of a secreted protein containing only a part of the first Ig-like module. The Fin-minor mutation would result in a nephrin molecule lacking a part of the cytosolic domain.

Several similarity comparison and protein structure prediction programs predicted that the NPHS1 protein would be a transmembrane protein of the immunoglobulin superfamily. There is a tentative 22-residue-long N-terminal signal peptide, an extracellular domain containing eight immunoglobulin-like domains, one fibronectin type III domain-like module, followed by a single putative transmembrane domain-like sequence, and a cytosolic C-terminal end. In spite of the presence of known structural modules (FIG. 4), the sequence identity with corresponding domains of proteins in the data base was relatively low. The tentative extracellular portion of the protein contains ten NXS or NXT consensus triplets for N-glycosylation. Furthermore, there are seven SG doublets, that are potential attachment sites for heparan sulfate.

Northern hybridization analysis carried out with poly(A) mRNA from four human embryonic and eight adult tissues revealed a high steady state level of the NPHS1 gene transcript in the kidney, but not notably in other tissues. (FIG. 2). In situ hybridization carried out on a kidney sample from a 23-week-old human embryo revealed intense expression signals in the glomeruli (FIG. 5 A). At higher magnification (FIG. 5 B), the signals could be seen in the periphery of mature and developing glomeruli, while the central mesangial regions are negative. It is apparent that the positive cells are epithelial podocytes. No specific signals were obtained with the antisense control probe.

Figure 5A:
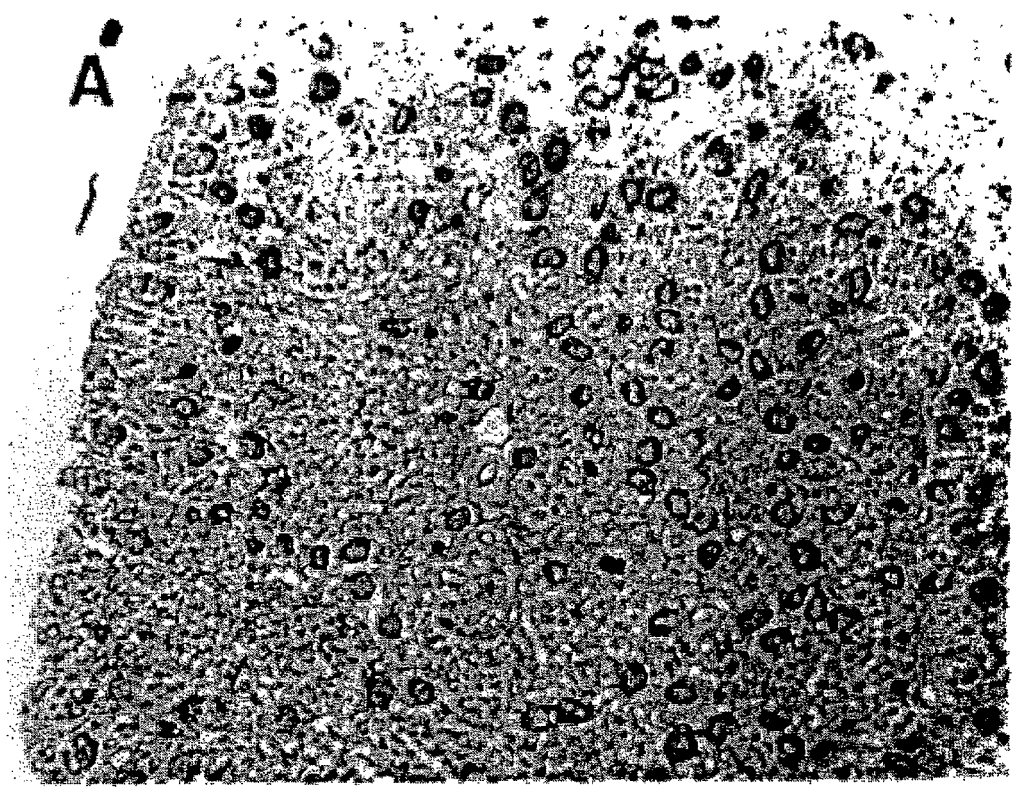
FIG. 5A, shows intense expression in glomeruli throughout the renal cortex, little if any specific expression being observed in other structures. (4× objective magnification).
Figure 5B:
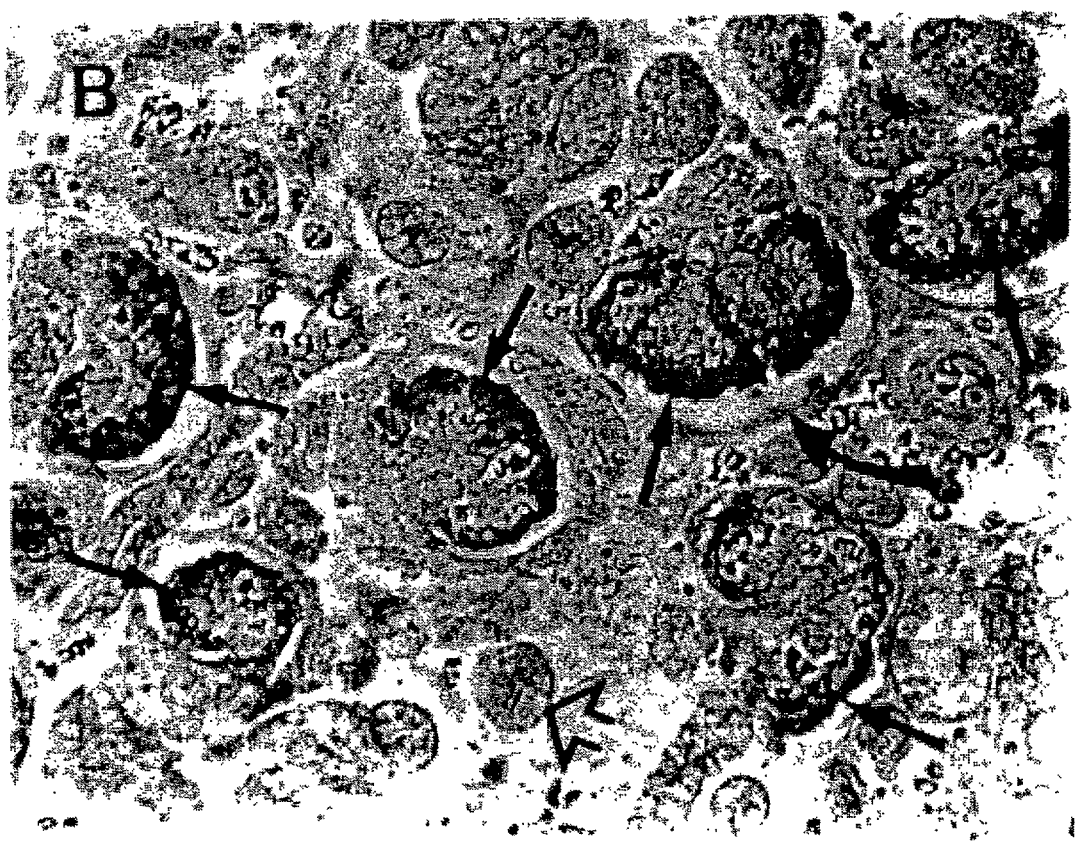
FIG. 5B, is a view at higher magnification which reveals intense expression in the periphery of individual glomeruli (straight arrows), probably mainly in epithelial cells. No expression is observed in the Bowman's capsule (bent arrow), proximal tubuli (open arrows), or endothelial cells of vessel walls. (20× objective magnification).

FIG. 5 illustrates expression of nephrin mRNA in human embryonic kidney by in situ hybridization FIG. 5A shows intense expression is seen in glomeruli throughout the renal cortex, little if any specific expression being observed in other structures. (4× objective magnification). FIG. 5B, Higher magnification reveals intense expression in the periphery of individual glomeruli (straight arrows), probably mainly in epithelial cells. No expression is observed in the Bowman's capsule (bent arrow), proximal tubuli (open arrows), or endothelial cells of vessel walls. (20× objective magnification).

EXAMPLE 5

The NPHS1 gene and its Gene Product Nephrin

Several lines of evidence obtained in the present study show that we have positionally cloned the gene affected in congenital nephrotic syndrome of the Finnish type. First, the defective gene is located in the critical 150 kb region on chromosome 19q13.1 to which the gene has been localized using linkage disequilibrium analyses (Kestilä et al., 1994b; Männikkö et al., 1995; Kestilä et al. manuscript). Second, the two mutations identified in the study were shown to be present, either as homozygous or compound heterozygous mutations, in 44 out of 49 Finnish patients studied. Four of the remaining patients had the major mutation in one allele, the mutation in the other allele being, as yet, unidentified. One patient who did not have either of the two mutations, has a unique haplotype and, therefore, probably carries a different mutation. Third, individuals homozygous or compound heterozygous for the mutations were not found in 230 control DNAs. Additional, indirect evidence was the strong and practically renal glomeruli-specific expression of the gene, which implies involvement of the gene product in glomerular development or function.

Identification of the NPHS1 gene

The present identification of the NPHS1 gene demonstrates the power of linkage disequilibrium analysis and direct DNA sequencing in the positional cloning of disease genes containing small mutations. Here, linkage disequilibrium mapping (Hästbacka et al., 1994) which when used with DNA from individuals of a homogenous population, such as the isolated Finnish population (de la Chapelle, 1993), was utilized to localize the NPHS1 gene to a 150 kb genomic segment. In order to find genes located in this region, the entire segment was first sequenced, and using a combination of exon prediction programs and homology comparison analyses we could construct remarkably accurate gene structures that were verified from cDNAs. These cDNAs could be isolated either with the use of EST clones or by using the predicted exon sequences to construct cDNAs by PCR from mRNA. In this manner we could quickly identify 11 genes within the 150 kb NPHS1 containing genomic segment. Since none of the genes was an obvious candidate for NPHS1, and no major gene rearrangements, such as deletions, insertions or inversions, were found in patient DNAs, search for small mutations had to be initiated, if necessary, in all the 11 genes. Having determined the exon and cDNA sequences for the genes, methods such as SSCP and DGGE, which are frequently used for identification of small mutations, were potential alternatives. However, our experience from the search for small mutations in Alport syndrome (Barker et al., 1990; Tryggvason, 1996) suggests that these methods can frequently yield false negatives. For example, SSCP analyses in quite large patient populations have revealed only a 35–50% mutation detection rate (Kawai et al., 1996, Knebelmann et al. 1996, Renieri et al., 1996), while our direct sequencing of PCR-amplified exon regions has yielded over 80% detection. We therefore decided to use direct sequencing of exon regions to find the NPHS1 mutations. Although we had to sequence numerous exons of several genes, this relatively soon resulted in the identification of two small mutations in one gene. We conclude that sequencing of even a large candidate gene region and direct sequencing of its genes is an attractive and, above all, reliable method to search for small mutations in positional cloning, particularly if only few mutations can be expected to be present.

Genetics of NPHS1

Crucial components in the successful positional cloning of the NPHS1 gene were the small isolated population, good clinical records and equal, high quality health care system which made it possible to reliably collect family samples. A typical situation in population isolates is that close to 100% of cases are caused by the same mutation, and this phenomenon can already be seen in haplotype analysis. Observed changes in the founder haplotype, caused by historical recombinations, can be used to restrict the critical chromosomal region to a short genomic segment. Thus, differences in the major NPHS1 haplotype 1-1-1-6-g-2-8-9 enabled substantial narrowing of the interval, leading to the isolation of the NPHS1 gene. The major NPHS1 mutation causes only 78% of cases, in contrast to many other "Finnish diseases" with 95–98% prevalence of major disease alleles (e.g. Ikonen et al., 1991). However, the two main NPHS1 mutations characterized in this study together represent 94% of Finnish cases.

Congenital nephrotic syndrome of the Finnish type is enriched in the Finnish population, but several cases can be found worldwide. Considerable immigration from Finland to Minnesota has also caused the spread of NPHS1 to the USA (Norio 1966; Mahan et al., 1984). In addition, several CNF cases have been diagnosed in different European countries, and linkage studies have supported association of analyzed families to the same chromosome 19 locus (Fuchshuber et al., 1996).

The identification of the NPHS1 gene and disease causing mutations have immediate clinical significance, as they have enabled the development of exact DNA-based diagnosis for NPHS1 and carrier screening. This is particularly important, as we have recently demonstrated that the screening method widely used in Finland for NPHS1 based on measurements of alpha-fetoprotein levels in amniotic fluid can lead to false positive results and subsequent abortions of healthy NPHS1 carriers (Männikkö et al., 1997).

Nephrin—a Glomerulus-specific Cell Adhesion Receptor

Due to the high association of expression and pathology with glomeruli, the proximal part of the nephron, we have named the NPHS1 gene product nephrin. The role of nephrin remains unknown, but it is likely to be an adhesion receptor and a signaling protein, as its domain structure resembles that of a large group of cell adhesion receptors belonging to the immunoglobulin superfamily (Brümmendott and Rathjen, 1994).

The Ig-like domains of nephrin are all of type C2 which is particularly found in proteins participating in cell-cell or cell-matrix interactions. Between the sixth and seventh Ig-like domains there is a spacer of about 130 residues containing an unpaired cysteine, and there is another unpaired cysteine in the fibronectin type III-like domain. Their SH groups could be involved in the formation of cis homo/heterodimers, participate in thioether or thioester bonds with unknown structures, or be buried within the domains, as suggested by Brümmendott and Rathjen (1994).

Data base searches revealed that the cytosolic domain that contains nine tyrosine residues of nephrin has no significant homology with other known proteins. However, sequence motifs surrounding tyrosines suggest that tyrosines 1176, 1192 and 1217 could become phosphorylated during ligand binding of nephrin (see, Songyang et al. 1993). In that case, binding sites for the SH2-domains of Src-family kinases, Abl-kinase, and an adaptor protein Nck might be created (tyrosines 1176 and 1192 are followed by the motif DEV, and tyrosine 1217 by DQV). The crucial role for the intracellular domain of nephrin is emphasized by the fact that the Fin-minor mutation which results in the loss of 132 out of 155 residues results in full blown NPHS1.

The pathogenesis of NPHS1 has been thought to primarily or secondarily involve the highly anionic glycosaminoglycans, as the content of such molecules that are considered important for the glomerular filtration process is reported to be decreased in the GBM in proteinuria (Kasinath and Kanwar, 1993). It cannot be excluded that nephrin is a proteoglycan, as it has several SG consensus sites for heparan sultate side chains, including the triplet SGD which is the major attachment sequence for the three large heparan sulfate side chains in the basement membrane proteoglycan perlecan (Noonan et al., 1991; Kallunki and Tryggvason, 1992; Dolan et al., 1997). However, thus far no Ig-like receptors have been reported to contain glycosaminoglycans.

How does nephrin function and what is its role in glomerular function? A vast majority of similar receptors interact with other membrane proteins in a homo- or heterophilic manner. However, some of the receptors have been shown to interact with extracellular matrix (ECM) proteins. For example, the myelin-associated glycoprotein MAG whose extracellular domain contains five Ig-like domains, interacts with different types of collagens and glycosaminoglycans (Fahrig et al., 1987). Furthermore, the axonal glycoprotein F11 and the deleted in colorectal cancer (DCC) protein have both been shown to bind tenascins and netrins, respectively (Zisch et al., 1992; Pesheva et al., 1993; Keino-Masu, 1996). Since it is possible that nephrin either binds another membrane protein or a protein of the ECM, which in this case would be the GBM, it will be important to localize nephrin by immunoelectron microscopy before embarking on the search for a specific ligand.

Whatever its function, the in situ hybridization analyses strongly suggested that nephrin is produced in glomerular epithelial cells that form the foot processes partially covering the outside of the glomerular capillaries. The ultimate filtration barrier for plasma macromolecules is located in the diaphragm covering the slit pores between the foot processes. In NPHS1 and nephrotic syndromes of other causes, fusion of the foot processes is a general finding, and the structure or function of the slit pores are somehow affected with proteinuria as a result. It is proposed that the plasma membrane protein nephrin is important for maintaining the integrity of the foot processes of glomerular epithelial cells, or is crucial for their anchorage to components of the GBM.

Conclusions

The identification of the NPHS1 gene will immediately find applications for diagnosis of the disease. Studies on the gene product nephrin, a putative cell adhesion and signaling receptor, may also provide a key to new fundamental knowledge on the molecular mechanisms of glomerular filtration, which despite decades of research are still poorly understood. As abnormal function of the filtration barrier is a major complication in many clinically important kidney diseases, such as diabetic nephropathy, nephrotic syndromes and glomerulonephritides, the present work is likely to have a more general impact on clinical nephrology. Immediate questions relate to the developmental expression and location of the protein, which would require the generation of antibodies and nucleotide probes for studies in animal and cell culture systems.

EXAMPLE 6

Genetic Screening for Basement Membrane Disease

With the identification and characterisation of nephrin as a critical component in basement membrane disease associated with glomerular nephropathy, it is now possible to screen individuals, both pre- and post-natal screening, for susceptibility for basement membrane disease by detecting mutated nephrin gene or protein. Such information will be useful to medical practitioners for the future diagnosis of disease conditions in screened individuals, and for planning preventative measures for the possible containment of future disease. Such information will be useful for the diagnosis of currently active disease conditions. The present invention allows for the diagnosis of currently active disease conditions, as being related to basement membrane disease by detecting mutated nephrin gene or protein. The discovery of the nephrin gene provides a means for detecting the presence of the nephrin gene in individuals, and for the determination of the presence of any mutations in said gene. Such means for detection comprises nucleic acids having the entire nephrin gene sequence, or fragments thereof which will specifically hybridize to said nephrin gene, or mRNA transcripts from said nephrin gene under stringent conditions. An additional means for detection of the nephrin gene and mutations therein comprise specific contiguous fragments of said gene, and complementary gene sequence, which can be combined for use as primers for amplifying the targeted gene sequence. Said means for detection of mutations in a nephrin gene also comprise direct hybridization of normal gene with target gene and subsequent detection of successful hybridization. In all cases, the target gene may be amplified or unamplified DNA or RNA isolated from the individual to be tested.

Antibody Screening of Tissues and Samples

By having the NPHS1 gene sequence, it is well within the skill of one in the art to use existing molecular biology and biochemical techniques to construct and use an expression vector which will produce recombinant nephrin protein, or fusion protein, purify this protein, and produce antibodies specifically reactive with nephrin. The expression of proteins in bacterial, yeast, insect and mammalian cells is known in the art. It is known in the art how to construct and use expression vectors in which the expressed gene contains one or more introns. The production of monoclonal antibodies is well known in the art, and the use of polyclonal and monoclonal antibodies for immunohistochemical detection of protein in tissue samples is a routine practice. A wide variety of detectable labels are available for use in immunohistochemical staining and immunoassays for detection of protein in samples such as homogenised tissue, blood, serum, urine or other bodily fluids.

One of ordinary skill in the art will be able to readily use the teachings of the present invention to design suitable assays and detection schemes for practising the screening methods contemplated by the present invention.

Gene Therapy

Given the teaching of the present invention, it will be possible to address deficiencies in Nephrin gene or protein by gene therapy or therapy using recombinant protein. Methods for the administration of protein and gene therapy are known in the art.

GenBank Accession Numbers

The accession numbers for the cosmid clones characterised are: F19541=U95090, R33502=AC002133, R28051=AD000864, F19399=AD000833, R31158=AD000827, R31874=AD000823. The accession for the nephrin cDNA sequence is AF035835.

One of ordinary skill in the art will be able to readily use the teachings of the present invention to design and construct suitable nucleic acid sequences which will be the functional equivalents of those disclosed. One of ordinary skill in the art will know that there exisits many allelic variants of the disclosed nucleic acid sequnences which still encode for a nephrin protein with equivalent function. The teaching of the present invention allows for the discovery of mutations in the nephrin gene and the modified protein therein encoded.

EXAMPLE 7

Screening for Small Molecule Therapeutics

With the identification and characterisation of nephrin as a critical component in kidney pathothgy and proteinuria, and thus implicated in many kidney diseases, it is now possible to screen for small molecule therapeutics using nephrin and the neprhin gene. Screening for such therapeutics can be accomplished by sequential selective screening for activity and molecules which specifically hybridize to nephrin, or which specifically effect the expression of the nephrin gene. Selective screening can be performed on pools of small molecule compounds generated by standard combinatorial chemistry, on known molecules, or in combination with computer modeling of the nephrin protein structure and rational drug design. Such methods and techniques are known in the art.

LITERATURE CITED

Altschul, S. F., Gish, W., Miller, W., Myers, E. W., and Lipman, D. J. (1990) Basic local alignment search tool. J. Mol. Biol. 215, 403–10

Appel, R. D., Bairoch, A. and Hochstrasser, D. F. (1994) A new generation of information retrieval tools for biologists: the example of the ExPASy WWW server. Trends Biochem. Sci. 19: 258–260

Barker, D., Hostikka, S. L., Zhou, J., Chow, L. T., Oliphant, A. R., Gerken, S. C., Gregory, M. C., Skolnick, M. H., Atkin, C. L. and Tryggvason, K. (1990) Identification of mutations in the COL4A5 collagen gene in Alport syndrome. Science 248, 1224–1227

Brümmendott, T., and Rathjen, F. G. (1994) Cell adhesion molecules 1: Immunoglobulin superfamily. Protein profile 1, 951–1058.

Burge, C. and Karlin, S. (1997) Prediction of complete gene structures in human genomic DNA. J. Mol. Biol. 268, 78–94.

de la Chapelle, A. (1993) Disease gene mapping in isolated human populations: the example of Finland. J. Med. Genet. 30:857–865

Dolan, M., Horchar, T., Rigatti, B., and Hassell, J. R. (1997) Identification of sites in domain I perlecan that regulate heparan sulfate synthesis. J. Biol. Chem. 272, 4316–4322

Fahrig, T., Landa, C., Pesheva, P., Kühn, K., and Schacher, M. (1987) Characterization of binding properties of the myelin-associated glycoprotein to extracellular matrix constituents. EMBO J. 6, 2875–2883.

Fuchshuber, A., Niaudet, P., Gribouval, O., Genevieve, J., Gubler, M-C., Broyer, M. and Antignac, C. (1996) Congenital nephrotic syndrome of the Finnish type: linkage to the locus in a non-Finnish population. Pediatr. Nephrol. 10: 135–138

Genetics Computer Group, Program manual for the Wisconsin Package, Version 9, December 1996, 575 Science Drive, Madison, Wis., USA 53711

Hästbacka, J., de la Chapelle, A., Mahtani, M. M., Clines, G., Reeve-Daly, M. P., Daly, M., Hamilton, B. A., Kusumi, K., Trivedi, B., Weaver, A., Coloma, A., Lovett, M., Buckler, A., Kaitila, I., and Lander, E. S. (1994) The diastrophic dysplasia gene encodes a novel sulfate transporter: positional cloning by fine-stucture linkage disequilibrium mapping. Cell 78, 1073–1087

Holmberg, C., Antikainen, M., Rönnholm, K., Ala-Houhala, M. and Jalanko, H. (1995) Management of congenital nephrotic syndrome of the Finnish type. Pediatr. Nephrol. 9: 87–93

Huttunen, N. P., Rapola, J., Vilska, J. and Hallman, N. (1980) Renal pathology in congenital nephrotic syndrome of the Finnish type: a quantitative light microscopic study on 50 patients. Int. J. Pediatr. Nephr. 1: 10–16

Ikonen, E., Baumann, M., Grön, K., Syvänen, A-C., Enomaa, N., Halila, R., Aula, P. and Peltonen, L. (1991) Aspartylglucosaminuria: cDNA encoding human aspartylglucosaminidase and the missense mutation causing the disease. EMBO J. 10: 51–58

Jurka, J., Klonowski, P., Dagman, V., Pelton, P. (1996) CENSOR—a program for identification and elimination of repetitive elements from DNA sequences. Computers and Chemistry Vol. 20 (No. 1): 119–122.

Kallunki, P., and Tryggvason, K. (1992) Human basement membrane heparan sulfate proteoglycan core protein: a 467 kD protein containing multiple domains resembling elements of the low density lipoprotein receptor, laminin, neural cell adhesion molecules, and epidermal growth factor. J. Cell Biol. 116, 559–571

Kasinath, B. S. and Kanwar, Y. S. (1993) Glomerular basement membrane: biology and physiology. In: Molecular and cellular aspects of basement membranes (D. Rorhbach and R. Timpl, eds), Academic Press, pp. 89–106.

Kawai, S., Nomura, S., Harano, T., Fukushima, T., & Osawa, G. (1996) The COL4A5 gene in Japanese Alport syndrome patients: spectrum of mutations of all exons. Kidney Int. 49, 814–822

Keino-Masu, K., Masu, M. Hinck, L., Leonardo, E. D., Chan, S. S. Y., Culotti, J. G., and Tessier-Lavigne, M. (1996) Cell 87, 175–185

Kestilä, M., Männikkö, M., Holmberg, C., Korpela, K., Savolainen, E. R., Peltonen, L. and Tryggvason, K. (1994a) Exclusion of eight genes as mutated loci in congenital nephrotic syndrome of the Finnish type. Kidney Int. 45, 986–990

Kestilä, M., Männikkö, M., Holmberg, C., Gyapay, G., Weissenbcah, J., Savolainen, E. R., Peltonen, L. and Tryggvason, K. (1994b) Congenital nephrotic syndrome of the Finnish type maps to the long arm of chromosome 19. Am. J. Hum. Genet. 54, 757–764

Knebelmann, B., Breillat, C., Forestier, L., Arrondel, C., Jacassier, D., et al. (1996) Spectrum of mutations in the COL4A5 collagen gene in X-linked Alport syndrome. Am. J., Hum. Genet. 59, 1221–1232

Koskimies, O. (1990) Genetics of congenital and early infantile nephrotic syndromes. In: Spitzer, A., Avner, E.

D. (eds) Inheritance of kidney and uritary tract diseases. Kluwer, Boston, Dordrecht and London, p. 131–138

Laine, J., Jalanko, H., Holthöfer, H., Krogerus, L., Rapola, J., von Willebrand, E., Lautenschlager, I., Salmela, K. and Holmberg, C. (1993) Post-transplantation nephrosis in congenital nephrotic syndrome of the Finnish type. Kidney Int. 44: 867–874

Lenkkeri, U., Kestilä, M., Lamerdin, J., McCready, P., Adamson, A., Olsen, A. and Tryggvason, K. Structure of the human amyloid precursor like protein gene APLP1 at 19q13.1. Human Genetics, in press Ljungberg, P., Jalanko, H., Holmberg, C. and Holthöfer, H. (1993) Congenital nephrosis of the Finnish type (CNF): matrix components of the glomerular basement membranes and of cultured mesangial cells. Histochem. J. 25: 606–612

Mahan, J. D., Mauer, S. M. Sibley, R. K. and Vernier, R. L. (1984) Congenital nephrotic syndrome: Evolution of medical management and results of renal transplantation. J. Pediatr. 105: 549–557

Männikkö, M., Kestilä, M., Holmberg, C., Norio, R., Ryynänen, M., Olsen, A., Peltonen, L. and Tryggvason, K. (1995) Fine mapping and haplotype analysis of the locus for congenital nephrotic syndrome on chromosome 19q13.1. Am. J. Hum. Genet. 57: 1377–1383

Männikkö, M., Kestilä, M., Lenkkeri, U., Alakurtti, H., Holmberg, C., Leisti, J., Salonen, R., Aula, P., Mustonen, A., Peltonen, L. and Tryggvason, K. (1997) Improved prenatal diagnosis of the congenital nephrotic syndrome of the Finnish type nased on DNA analysis, Kidney Int. 51: 868–872

Martin, P., Heiskari, N., Hertz, J.-M-, Atkin, C., Barker, D., et al. Survey of mutations in the COL4A5 collagen gene in patients with suspected Alport syndrome: PCR amplification and direct sequencing of all 51 exon regions reveals over 80 mutation detection rate. (manuscript).

Noonan, D. M., Fulle, A., Valente, P., Cai, S., Horigan, E., Sasaki, M., Yamada, Y., and Hassell, J. R. (1991) The complete sequence of perlecan, a basement membrane heparan sulfate proteoglycan, reveals extensive similarity with laminin A chain, low density lipoprotein receptor, and the neural cell adhesion molecule. J. Biol. Chem. 266, 22939–22947

Norio, R. (1966) Heredity on the congenital nephrotic syndrome. Ann. Paediatr. Fenn. 12 (suppl 27):1–94

Olsen, A., Georgescu, A., Johnson, S. and Carrano, A. V. (1996) Assembly of a 1-Mb restriction-mapped cosmid contig spanning the candidate region for Finnish congenital nephrosis (NPHS1) in 19q13.1. Genomics 34:223–225

Pesheva, P., Gennarini, G., Goridis, C., and Schacher, M. (1993) The F3/11 cell adhesion molecule mediates the repulsion of neurons by the extracellular matrix glycoprotein J1–160/180. Neuron 10, 69–82

Pekkarinen P., Kestilä M., Hakola P., Järvi O., Tryggvason, K. and Palotie L. Fine-scale mapping of the PLO-SL locus. (manuscript)

Rapola, J., Huttunen, N. P. and Hallman, N. (1992) Congenital and infantile nephrotic syndrome. In: Edelman C M (ed.) Pediatric Kidney Disease. $2^{nd}$ ed. Little, Brown and Company, Boston. Vol 2: 1291–1305

Renieri, A., Bruttini, M., Galli, L., Zanelli, P., Neri, T., et al. (1996) X-linked Alport syndrome: an SSCP-based mutation survey over all 51 exons of the COL4A5 gene. Am. J. Hum. Genet. 58, 1192–1204

Solovyev, V. V., Salamov, A. A., Lawrence, C. B. (1994) Predicting internal exons by oligonucleotide composition and discriminant analysis of spliceable open reading frames. Nucl. Acids Res. 22(24): 5156–5163

Tryggvason, K. (1996) Mutations in type IV collagen genes in Alport syndrome. In: Molecular pathology and Genetics of Alport syndrome (ed. K. Tryggvason). Contrib. Nephrol., 117, 154–171, Karger, Basel Tryggvason, K. and Kouvalainen, K. (1975) Number of nephrons in normal human kidneys and kidneys of patients with the congenital nephrotic syndrome. Nephron 15: 62–68

Uberbacher, E. C. and Mural, R. J. (1991) Locating protein-coding regions in human DNA sequences by a multiple sensor-neural network approach, Proc. Natl Acad. Sci. USA 88: 11261–11265

Zisch, A. H., D'Allessandri, L., Ranscht, B., Falchetto, R., Winterhalter, K. H., and Vaughan, L. (1992) Neuronal cell adhesion molecule contactin/F11 binds to tenascin via its immunoglobulin-like domains. J. Cell Biol. 119, 203–213

---

We claim:

1. A method for diagnosing the presence of a basement membrane disease in an individual, comprising detecting the presence of a mutation in exon 2 of the NPHS1 gene comprising the nucleic acid sequence of SEQ ID NO:1, wherein the mutation results in a premature stop codon in the exon and, wherein the mutation in exon 2 comprises a two base pair deletion of nucleotides 121–122 of the NPHS1 gene.

2. The method of claim 1, wherein the NPHS 1 gene is amplified prior to detecting the presence of the mutation in exon 2.

3. The method of claim 2, wherein the amplification is by PCR and the primers used for amplification specifically amplify the exon 2 region of the NPHS1 gene.

4. The method of claim 3, wherein the primers used for amplification comprise DNA sequence comprising SEQ ID NO:3 or SEQ ID NO:4.

5. A method for diagnosing the presence of a basement membrane disease in an individual, comprising detecting the presence of a mutation in exon 26 of the NPHS1 gene comprising the nucleic acid sequence of SEQ ID NO:1, wherein the mutation in exon 26 comprises a single base change, and wherein the single base pair change results in the nonsense mutation CGA→TGA.

6. The method of claim 5, wherein the NPHS1 gene is amplified prior to detecting the presence of the mutation in exon 26.

7. The method of claim 6, wherein the amplification is by PCR and the primers used for amplification specifically amplify the exon 26 region of the NPHS1 gene.

8. The method of claim 7, wherein the primers used for amplification comprise DNA sequences comprising SEQ ID NO:5 or SEQ ID NO:6.

9. The method of claim 8, wherein a novel restriction site is detected in the amplified product.

10. The method of claim 9, wherein the novel restriction site is susceptible to digestion with Dd eI.

11. A method of determining whether an individual is at risk for developing a congenital nephrotic syndrome of the Finnish Type, comprising analyzing a nucleic acid sample containing the HPHS1 gene comprising the nucleic acid sequence of SEQ ID NO:1; wherein the method comprises analyzing the exon 2 region of the NPHS1 gene, wherein an individual at risk for developing a congenital nephrotic syndrome has a mutation in exon 2, wherein the mutation in exon 2 comprises a two base pair deletion of nucletides 121–122 of the NPHS1 gene.

12. The method of claim 11 wherein the NPHS1 gene is amplified prior to detecting the presence of the mutation in exon 2.

13. The method of claim 12, wherein the amplification is by PCR and the primers used for amplification specifically amplify the exon 2 region of the NPHS1 gene.

14. The method of claim 13, wherein the primers used for amplification comprise DNA sequences selected from the group consisting of SEQ ID NO:3 or SEQ ID NO:4.

15. A method of determining whether an individual is at risk for developing a congenital neprotic syndrome of the Finnjsh Type, comprising analyzing a nucleic acid sample containing the NPHS1 gene comprising the nucleic acid sequence of SEQ ID NO:1 wherein the method comprises analyzing the exon 26 region of the NPHS1 gene, wherein an individual at risk for developing a congenital nephrotic syndrome has at least one mutation in exon 26, wherein the mutation in exon 26 comprises a single base pair change and, wherein the single base pair change results in the nonsense mutation CGA→TGA.

16. The method of claim 15, wherein the NPHS1 gene is amplified prior to detecting the presence of the mutation in exon 26.

17. The method of claim 16, wherein the amplification is by PCR and the primers used for amplification specifically amplify the exon 26 region of the NPHS1 gene.

18. The method of claim 17, wherein the primers used for amplification comprise DNA sequences selected from the group consisting of SEQ ID NO:5 and SEQ ID NO:6.

19. The method of claim 18, wherein a novel restriction site is detected in the amplified product.

20. The method of claim 19, wherein the novel restriction site is susceptible to digestion with DdeI.

21. A method for determining that an individual is not at risk for developing congenital nephritic syndrome of the Finnish Type, wherein the syndrome is associated with a mutation in exon 2 or exon 26 of the NPHS1 gene, wherein the method comprises analyzing the exon 2 or exon 26 region of the NPHS1 gene comprising the nucleic acid sequence of SEQ ID NO:1, wherein the individual not at risk for developing the syndrome does not have a mutation in exon 2 or exon 26, wherein the mutation in exon 2 comprises a two base pair deletion of nucleotides 121–122 of the NPHS1 gene, and the mutation in exon 26 comprises a single base change resulting in the nonsense mutation CGA→TGA.

22. The method of claim 21, wherein the NPHS1 gene is amplified prior to analysis.

23. The method of claim 22, wherein the amplification is PCR amplification using primers comprising a DNA sequence selected from the group consisting of: SEQ ID NO:3, SEQ ID NO:4, and SEQ ID NO:6.

24. A method for detecting the presence or absence of a mutation in the NPHS1 gene, comprising the steps of:
   analyzing a nucleic acid test sample containing the NPHS1 gene encoded for by the nucleic acid sequence of SEQ ID NO:1 for at least one mutation in exon 2 or exon 26 of the gene;
   comparing the results of the analysis of the test sample of step a) with the results of the analysis of a control sample, wherein the control sample comprises a NPHS1 gene encoded for by the nucleic acid sequence of SEQ ID NO:1 without a mutation in exon 2 or exon 26; and
   determining the presence or absence of at least one mutation in exon 2 or exon 26 in the test sample.

25. The method of claim 24, wherein the mutation in exon 2 is a two base pair deletion and the mutation in exon 26 is a single base pair change, wherein either mutation results in a premature stop codon in the exon.

26. The method of claim 24, wherein the NPHS1 gene is amplified prior to analysis.

27. The method of claim 26, wherein the amplification is PCR amplification using primers comprising a DNA sequence selected from the group consisting of: SEQ ID NO:3, SEQ ID NO:4, and SEQ ID NO:5, and SEQ ID NO:6.

* * * * *

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 4285 base pairs
      (B) TYPE: nucleic acid
      (C) STRANDEDNESS: single
      (D) TOPOLOGY: Not Relevant (ii) MOLECULE TYPE: cDNA (ix) FEATURE:
      (A) NAME/KEY: sig_peptide
      (B) LOCATION: 1..66
      (D) OTHER INFORMATION: /note= "putative signal peptide"

```
        (ix) FEATURE:
              (A) NAME/KEY: CDS
              (B) LOCATION: 1..3723

(ix) FEATURE:
              (A) NAME/KEY: mat_peptide
              (B) LOCATION: 67..3723

(ix) FEATURE:
              (A) NAME/KEY: misc_feature
              (B) LOCATION: 121..122
              (D) OTHER INFORMATION: /note= "deletion mutation
                  FIN-Major"

(ix) FEATURE:
              (A) NAME/KEY: misc_feature
              (B) LOCATION: 3800..3804
              (D) OTHER INFORMATION: /note= "nonsense mutation in exon
                  26 FIN-Minor"

(ix) FEATURE:
              (A) NAME/KEY: misc_feature
              (B) LOCATION: 3178..3258
              (D) OTHER INFORMATION: /note= "putative transmembrane
                  domain"

(xi) SEQUENCE DESCRIPTION: SEQ ID NO: 1:

ATG GCC CTG GGG ACG ACG CTC AGG GCT TCT CTC CTG CTC CTG GGG CTG        48
Met Ala Leu Gly Thr Thr Leu Arg Ala Ser Leu Leu Leu Leu Gly Leu
-22     -20             -15                 -10

CTG ACT GAA GGC CTG GCG CAG TTG GCG ATT CCT GCC TCC GTT CCC CGG        96
Leu Thr Glu Gly Leu Ala Gln Leu Ala Ile Pro Ala Ser Val Pro Arg
     -5              1               5                       10

GGC TTC TGG GCC CTG CCT GAA AAC CTG ACG GTG GTG GAG GGG GCC TCA       144
Gly Phe Trp Ala Leu Pro Glu Asn Leu Thr Val Val Glu Gly Ala Ser
                15                  20                  25

GTG GAG CTG CGT TGT GGG GTC AGC ACC CCT GGC AGT GCG GTG CAA TGG       192
Val Glu Leu Arg Cys Gly Val Ser Thr Pro Gly Ser Ala Val Gln Trp
            30                  35                  40

GCC AAA GAT GGG CTG CTC CTG GGC CCC GAC CCC AGG ATC CCA GGC TTC       240
Ala Lys Asp Gly Leu Leu Leu Gly Pro Asp Pro Arg Ile Pro Gly Phe
        45                  50                  55

CCG AGG TAC CGC CTG GAA GGG GAC CCT GCT AGA GGT GAA TTC CAC CTG       288
Pro Arg Tyr Arg Leu Glu Gly Asp Pro Ala Arg Gly Glu Phe His Leu
        60                  65                  70

CAC ATC GAG GCC TGT GAC CTC AGC GAT GAC GCG GAG TAT GAG TGC CAG       336
His Ile Glu Ala Cys Asp Leu Ser Asp Asp Ala Glu Tyr Glu Cys Gln
75              80                  85                  90

GTC GGC CGC TCT GAG ATG GGG CCC GAG CTC GTG TCT CCC AGA GTG ATC       384
Val Gly Arg Ser Glu Met Gly Pro Glu Leu Val Ser Pro Arg Val Ile
                95                 100                 105

CTC TCC ATC CTG GTT CCT CCC AAG CTG CTC CTG CTG ACC CCA GAG GCA       432
Leu Ser Ile Leu Val Pro Pro Lys Leu Leu Leu Leu Thr Pro Glu Ala
            110                 115                 120

GGC ACC ATG GTC ACC TGG GTA GCT GGG CAG GAG TAC GTG GTC AAC TGT       480
Gly Thr Met Val Thr Trp Val Ala Gly Gln Glu Tyr Val Val Asn Cys
        125                 130                 135

GTG TCT GGG GAC GCG AAG CCA GCA CCT GAC ATC ACC ATT CTC CTG AGT       528
Val Ser Gly Asp Ala Lys Pro Ala Pro Asp Ile Thr Ile Leu Leu Ser
140                 145                 150

GGA CAG ACA ATA TCT GAC ATC TCT GCA AAC GTG AAC GAG GGC TCC CAG       576
Gly Gln Thr Ile Ser Asp Ile Ser Ala Asn Val Asn Glu Gly Ser Gln
155                 160                 165                 170

CAG AAA CTC TTC ACT GTG GAG GCC ACA GCC AGG GTG ACA CCC CGG AGC       624
Gln Lys Leu Phe Thr Val Glu Ala Thr Ala Arg Val Thr Pro Arg Ser
                175                 180                 185
```

-continued

| | | |
|---|---|---|
| TCA GAT AAT AGG CAG TTG CTG GTC TGT GAG GCG TCT AGC CCA GCA CTG<br>Ser Asp Asn Arg Gln Leu Leu Val Cys Glu Ala Ser Ser Pro Ala Leu<br>190 195 200 | | 672 |
| GAG GCC CCC ATC AAG GCC TCA TTC ACC GTG AAT GTT CTG TTC CCT CCA<br>Glu Ala Pro Ile Lys Ala Ser Phe Thr Val Asn Val Leu Phe Pro Pro<br>205 210 215 | | 720 |
| GGA CCC CCT GTC ATC GAG TGG CCA GGC CTG GAT GAG GGG CAC GTG CGG<br>Gly Pro Pro Val Ile Glu Trp Pro Gly Leu Asp Glu Gly His Val Arg<br>220 225 230 | | 768 |
| GCA GGA CAG AGC TTG GAG CTG CCG TGC GTG GCC CGA GGG GGT AAT CCC<br>Ala Gly Gln Ser Leu Glu Leu Pro Cys Val Ala Arg Gly Gly Asn Pro<br>235 240 245 250 | | 816 |
| TTA GCC ACA CTG CAG TGG CTG AAG AAT GGC CAG CCG GTG TCC ACA GCG<br>Leu Ala Thr Leu Gln Trp Leu Lys Asn Gly Gln Pro Val Ser Thr Ala<br>255 260 265 | | 864 |
| TGG GGC ACA GAG CAC ACC CAG GCG GTG GCC CGC AGT GTG CTG GTG ATG<br>Trp Gly Thr Glu His Thr Gln Ala Val Ala Arg Ser Val Leu Val Met<br>270 275 280 | | 912 |
| ACC GTG AGG CCA GAA GAC CAT GGA GCG CAG CTC AGC TGC GAG GCC CAC<br>Thr Val Arg Pro Glu Asp His Gly Ala Gln Leu Ser Cys Glu Ala His<br>285 290 295 | | 960 |
| AAC AGC GTG TCT GCA GGG ACC CAG GAG CAC GGC ATC ACA CTG CAG GTC<br>Asn Ser Val Ser Ala Gly Thr Gln Glu His Gly Ile Thr Leu Gln Val<br>300 305 310 | | 1008 |
| ACC TTT CCC CCT AGT GCC ATT ATT ATC TTG GGA TCT GCA TCC CAG ACT<br>Thr Phe Pro Pro Ser Ala Ile Ile Ile Leu Gly Ser Ala Ser Gln Thr<br>315 320 325 330 | | 1056 |
| GAG AAC AAG AAC GTG ACA CTC TCC TGT GTC AGC AAG TCC AGT CGC CCG<br>Glu Asn Lys Asn Val Thr Leu Ser Cys Val Ser Lys Ser Ser Arg Pro<br>335 340 345 | | 1104 |
| CGG GTT CTG CTA CGA TGG TGG CTG GGC TGG CGG CAG CTG CTG CCC ATG<br>Arg Val Leu Leu Arg Trp Trp Leu Gly Trp Arg Gln Leu Leu Pro Met<br>350 355 360 | | 1152 |
| GAG GAG ACA GTC ATG GAT GGA CTG CAT GGC GGT CAC ATC TCC ATG TCC<br>Glu Glu Thr Val Met Asp Gly Leu His Gly Gly His Ile Ser Met Ser<br>365 370 375 | | 1200 |
| AAC CTG ACA TTC CTG GCG CGG CGG GAG GAC AAC GGT CTG ACC CTC ACA<br>Asn Leu Thr Phe Leu Ala Arg Arg Glu Asp Asn Gly Leu Thr Leu Thr<br>380 385 390 | | 1248 |
| TGT GAG GCC TTC AGT GAA GCC TTC ACC AAG GAG ACC TTC AAG AAG TCG<br>Cys Glu Ala Phe Ser Glu Ala Phe Thr Lys Glu Thr Phe Lys Lys Ser<br>395 400 405 410 | | 1296 |
| CTC ATC CTG AAC GTA AAA TAT CCC GCC CAG AAA CTG TGG ATT GAG GGT<br>Leu Ile Leu Asn Val Lys Tyr Pro Ala Gln Lys Leu Trp Ile Glu Gly<br>415 420 425 | | 1344 |
| CCC CCA GAG GGC CAG AAG CTC CGG GCT GGG ACC CGG GTG AGG CTG GTG<br>Pro Pro Glu Gly Gln Lys Leu Arg Ala Gly Thr Arg Val Arg Leu Val<br>430 435 440 | | 1392 |
| TGT TTG GCT ATC GGG GGC AAC CCA GAG CCC TCC CTC ATG TGG TAC AAG<br>Cys Leu Ala Ile Gly Gly Asn Pro Glu Pro Ser Leu Met Trp Tyr Lys<br>445 450 455 | | 1440 |
| GAC TCG CGC ACC GTG ACC GAG TCG CGG CTG CCG CAG GAG TCG CGG CGC<br>Asp Ser Arg Thr Val Thr Glu Ser Arg Leu Pro Gln Glu Ser Arg Arg<br>460 465 470 | | 1488 |
| GTG CAT CTC GGC AGC GTG GAG AAA TCT GGG AGC ACC TTC TCC CGA GAG<br>Val His Leu Gly Ser Val Glu Lys Ser Gly Ser Thr Phe Ser Arg Glu<br>475 480 485 490 | | 1536 |
| CTG GTG CTG GTC ACA GGG CCG TCG GAC AAC CAG GCC AAG TTC ACG TGC<br>Leu Val Leu Val Thr Gly Pro Ser Asp Asn Gln Ala Lys Phe Thr Cys<br>495 500 505 | | 1584 |

```
AAG GCT GGA CAG CTC AGC GCG TCC ACG CAG CTG GCG GTG CAG TTT CCC       1632
Lys Ala Gly Gln Leu Ser Ala Ser Thr Gln Leu Ala Val Gln Phe Pro
                510                 515                 520

CCA ACT AAC GTG ACG ATC CTG GCC AAC GCA TCC GCA CTG CGC CCG GGA       1680
Pro Thr Asn Val Thr Ile Leu Ala Asn Ala Ser Ala Leu Arg Pro Gly
                525                 530                 535

GAC GCC TTA AAC TTG ACA TGC GTC AGC GTC AGC AGC AAT CCG CCG GTC       1728
Asp Ala Leu Asn Leu Thr Cys Val Ser Val Ser Ser Asn Pro Pro Val
540                 545                 550

AAC TTG TCC TGG GAC AAG GAA GGG GAG AGG CTG GAG GGC GTG GCC GCC       1776
Asn Leu Ser Trp Asp Lys Glu Gly Glu Arg Leu Glu Gly Val Ala Ala
555                 560                 565                 570

CCA CCC CGG AGA GCC CCA TTC AAA GGC TCC GCC GCC GCC AGG AGC GTC       1824
Pro Pro Arg Arg Ala Pro Phe Lys Gly Ser Ala Ala Ala Arg Ser Val
                575                 580                 585

CTT CTG CAA GTG TCA TCC CGC GAT CAT GGC CAG CGC GTG ACC TGC CGC       1872
Leu Leu Gln Val Ser Ser Arg Asp His Gly Gln Arg Val Thr Cys Arg
                590                 595                 600

GCC CAC AGC GCC GAG CTC CGC GAA ACC GTG AGC TCC TTC TAT CGC CTC       1920
Ala His Ser Ala Glu Leu Arg Glu Thr Val Ser Ser Phe Tyr Arg Leu
                605                 610                 615

AAC GTA CTG TAC CGT CCA GAG TTC CTG GGG GAG CAG GTG CTG GTG GTG       1968
Asn Val Leu Tyr Arg Pro Glu Phe Leu Gly Glu Gln Val Leu Val Val
                620                 625                 630

ACC GCG GTG GAG CAG GGC GAG GCG TTG CTG CCC GTG TCC GTG TCC GCT       2016
Thr Ala Val Glu Gln Gly Glu Ala Leu Leu Pro Val Ser Val Ser Ala
635                 640                 645                 650

AAC CCC GCC CCC GAG GCC TTC AAC TGG ACC TTC CGC GGC TAT CGC CTC       2064
Asn Pro Ala Pro Glu Ala Phe Asn Trp Thr Phe Arg Gly Tyr Arg Leu
                655                 660                 665

AGT CCA GCG GGC GGC CCC CGG CAT CGC ATC CTG TCC AGC GGG GCT CTG       2112
Ser Pro Ala Gly Gly Pro Arg His Arg Ile Leu Ser Ser Gly Ala Leu
                670                 675                 680

CAT CTG TGG AAT GTG ACC CGC GCG GAC GAC GGC CTC TAT CAG CTG CAC       2160
His Leu Trp Asn Val Thr Arg Ala Asp Asp Gly Leu Tyr Gln Leu His
                685                 690                 695

TGC CAG AAC TCT GAG GGC ACC GCG GAA GCG CGG CTG CGG CTG GAC GTG       2208
Cys Gln Asn Ser Glu Gly Thr Ala Glu Ala Arg Leu Arg Leu Asp Val
700                 705                 710

CAC TAT GCT CCC ACC ATC CGT GCC CTC CAG GAC CCC ACT GAG GTG AAC       2256
His Tyr Ala Pro Thr Ile Arg Ala Leu Gln Asp Pro Thr Glu Val Asn
715                 720                 725                 730

GTC GGG GGT TCT GTG GAC ATA GTC TGC ACT GTC GAT GCC AAT CCC ATC       2304
Val Gly Gly Ser Val Asp Ile Val Cys Thr Val Asp Ala Asn Pro Ile
                735                 740                 745

CTC CCG GGC ATG TTC AAC TGG GAG AGA CTG GGA GAA GAT GAG GAG GAC       2352
Leu Pro Gly Met Phe Asn Trp Glu Arg Leu Gly Glu Asp Glu Glu Asp
                750                 755                 760

CAG AGC CTG GAT GAC ATG GAG AAG ATA TCC AGG GGA CCA ACG GGG CGC       2400
Gln Ser Leu Asp Asp Met Glu Lys Ile Ser Arg Gly Pro Thr Gly Arg
                765                 770                 775

CTG CGG ATT CAC CAT GCC AAA CTG GCC CAG GCT GGC GCT TAC CAG TGC       2448
Leu Arg Ile His His Ala Lys Leu Ala Gln Ala Gly Ala Tyr Gln Cys
                780                 785                 790

ATT GTG GAC AAT GGG GTG GCG CCT CCA GCA CGA CGG CTG CTC CGT CTT       2496
Ile Val Asp Asn Gly Val Ala Pro Pro Ala Arg Arg Leu Leu Arg Leu
795                 800                 805                 810

GTT GTC AGA TTT GCC CCC CAG GTG GAG CAC CCC ACT CCC CTA ACT AAG       2544
Val Val Arg Phe Ala Pro Gln Val Glu His Pro Thr Pro Leu Thr Lys
                815                 820                 825
```

-continued

```
GTG GCT GCA GCT GGA GAC AGC ACC AGT TCT GCC ACC CTC CAC TGC CGT    2592
Val Ala Ala Ala Gly Asp Ser Thr Ser Ser Ala Thr Leu His Cys Arg
            830                 835                 840

GCC CGA GGT GTC CCC AAC ATC GTT TTC ACT TGG ACA AAA AAC GGG GTC    2640
Ala Arg Gly Val Pro Asn Ile Val Phe Thr Trp Thr Lys Asn Gly Val
        845                 850                 855

CCT CTG GAT CTC CAA GAT CCC AGG TAC ACG GAG CAC ACA TAC CAC CAG    2688
Pro Leu Asp Leu Gln Asp Pro Arg Tyr Thr Glu His Thr Tyr His Gln
860                 865                 870

GGT GGT GTC CAC AGC AGC CTC CTG ACC ATT GCC AAC GTG TCT GCC GCC    2736
Gly Gly Val His Ser Ser Leu Leu Thr Ile Ala Asn Val Ser Ala Ala
875                 880                 885                 890

CAG GAT TAC GCC CTC TTC ACA TGT ACA GCC ACC AAC GCC CTT GGC TCG    2784
Gln Asp Tyr Ala Leu Phe Thr Cys Thr Ala Thr Asn Ala Leu Gly Ser
            895                 900                 905

GAC CAA ACC AAC ATT CAA CTT GTC AGC ATC AGC CGC CCT GAC CCT CCA    2832
Asp Gln Thr Asn Ile Gln Leu Val Ser Ile Ser Arg Pro Asp Pro Pro
            910                 915                 920

TCA GGA TTA AAG GTT GTG AGT CTG ACC CCA CAC TCC GTG GGG CTG GAG    2880
Ser Gly Leu Lys Val Val Ser Leu Thr Pro His Ser Val Gly Leu Glu
        925                 930                 935

TGG AAG CCT GGC TTT GAT GGG GGC CTG CCA CAG AGG TTC TGC ATC AGG    2928
Trp Lys Pro Gly Phe Asp Gly Gly Leu Pro Gln Arg Phe Cys Ile Arg
    940                 945                 950

TAT GAG GCC CTG GGG ACT CCA GGG TTC CAC TAT GTG GAT GTC GTA CCA    2976
Tyr Glu Ala Leu Gly Thr Pro Gly Phe His Tyr Val Asp Val Val Pro
955                 960                 965                 970

CCC CAG GCC ACC ACC TTC ACG CTG ACT GGT CTA CAG CCT TCT ACA AGA    3024
Pro Gln Ala Thr Thr Phe Thr Leu Thr Gly Leu Gln Pro Ser Thr Arg
            975                 980                 985

TAC AGG GTC TGG CTG CTG GCC AGT AAT GCC TTG GGG GAC AGT GGA CTG    3072
Tyr Arg Val Trp Leu Leu Ala Ser Asn Ala Leu Gly Asp Ser Gly Leu
        990                 995                 1000

GCT GAC AAA GGG ACC CAG CTT CCC ATC ACT ACC CCA GGT CTC CAC CAG    3120
Ala Asp Lys Gly Thr Gln Leu Pro Ile Thr Thr Pro Gly Leu His Gln
        1005                1010                1015

CCT TCT GGA GAA CCT GAA GAC CAG CTG CCC ACA GAG CCA CCT TCA GGA    3168
Pro Ser Gly Glu Pro Glu Asp Gln Leu Pro Thr Glu Pro Pro Ser Gly
    1020                1025                1030

CCC TCG GGG CTG CCC CTG CTG CCT GTG CTG TTC GCT CTT GGG GGG CTT    3216
Pro Ser Gly Leu Pro Leu Leu Pro Val Leu Phe Ala Leu Gly Gly Leu
1035                1040                1045                1050

CTG CTC CTC TCC AAT GCC TCC TGT GTC GGG GGG GTC CTC TGG CAG CGG    3264
Leu Leu Leu Ser Asn Ala Ser Cys Val Gly Gly Val Leu Trp Gln Arg
            1055                1060                1065

AGA CTC AGG CGT CTT GCT GAG GGC ATC TCA GAG AAG ACA GAG GCA GGG    3312
Arg Leu Arg Arg Leu Ala Glu Gly Ile Ser Glu Lys Thr Glu Ala Gly
        1070                1075                1080

TCG GAA GAG GAC CGA GTC AGG AAC GAA TAT GAG GAG AGC CAG TGG ACA    3360
Ser Glu Glu Asp Arg Val Arg Asn Glu Tyr Glu Glu Ser Gln Trp Thr
    1085                1090                1095

GGA GAG CGG GAC ACT CAG AGC TCC ACG GTC AGC ACA ACA GAG GCA GAG    3408
Gly Glu Arg Asp Thr Gln Ser Ser Thr Val Ser Thr Thr Glu Ala Glu
1100                1105                1110

CCG TAT TAC CGC TCC CTG AGG GAC TTC AGC CCC CAG CTG CCC CCG ACG    3456
Pro Tyr Tyr Arg Ser Leu Arg Asp Phe Ser Pro Gln Leu Pro Pro Thr
1115                1120                1125                1130

CAG GAG GAG GTG TCT TAT TCC CGA GGT TTC ACA GGT GAA GAT GAG GAT    3504
Gln Glu Glu Val Ser Tyr Ser Arg Gly Phe Thr Gly Glu Asp Glu Asp
            1135                1140                1145
```

```
ATG GCC TTC CCT GGG CAC TTG TAT GAT GAG GTA GAA AGA ACG TAC CCC      3552
Met Ala Phe Pro Gly His Leu Tyr Asp Glu Val Glu Arg Thr Tyr Pro
        1150                1155                1160

CCG TCT GGA GCC TGG GGA CCC CTC TAC GAT GAA GTG CAG ATG GGA CCC      3600
Pro Ser Gly Ala Trp Gly Pro Leu Tyr Asp Glu Val Gln Met Gly Pro
        1165                1170                1175

TGG GAC CTC CAC TGG CCT GAA GAC ACA TAT CAG GAT CCA AGA GGA ATC      3648
Trp Asp Leu His Trp Pro Glu Asp Thr Tyr Gln Asp Pro Arg Gly Ile
        1180                1185                1190

TAT GAC CAG GTG GCC GGA GAC TTG GAC ACT CTG GAA CCC GAT TCT CTG      3696
Tyr Asp Gln Val Ala Gly Asp Leu Asp Thr Leu Glu Pro Asp Ser Leu
1195                1200                1205                1210

CCC TTC GAG CTG AGG GGA CAT CTG GTG TAAGAGCCCT CTCAACCCCA            3743
Pro Phe Glu Leu Arg Gly His Leu Val
                1215

TTGTCCTGCA CCTGCAGGAA TTTACACTCC ACTGGTCTCT CTCATTACAG CCTGGGCC      3803

GCTGGTTAGG TGAGCTCCAT AAAACCCAAA GGGACTTGGT GTCAGGAGAG GACATGGA      3863

GGGCTGAGTG ACAGAGATGG TTCAGCTGGT ACCAGAGTAG AAACAAGGTG CATCCTGG      3923

TTGGCTTTAG AAACTAAACT TCTCCAAAAG GACAGGGCA ATTGTAAACG TCGTCTCA       3983

AATGAAATGC TGCCGGGTGC GGTGACTCAC GCCTATAATC CCAGCACTTT GGGAGGCT      4043

GGCGGGTGGA TCACCTGAGG TCAGGAGTTC GAGACCAGCC TGGCCAACAT GGTAAAAC      4103

CATTTCTACT AAAAATATAA AAAATTAGCC AGGAGTAGTG GCGCATGCCT GTAGTCCC      4163

CTACTTGGGA GGCTGATGCA TGAGAATTGC TTGAACCCAG GAGGCGGAGG TTGCAGTG      4223

CTGAGATCAC GCCACTGCAC TCCAGCCTGG GCGACAGAGC GAGATTCTGT CTCAAAAA      4283

AA                                                                   4285

(2) INFORMATION FOR SEQ ID NO: 2:

(i) SEQUENCE CHARACTERISTICS:
        (A) LENGTH: 1241 amino acids
        (B) TYPE: amino acid
        (D) TOPOLOGY: linear (ii) MOLECULE TYPE: protein (xi) SEQUENCE DESCRIPTION: SEQ ID NO: 2:

Met Ala Leu Gly Thr Thr Leu Arg Ala Ser Leu Leu Leu Gly Leu
-22         -20                 -15                 -10

Leu Thr Glu Gly Leu Ala Gln Leu Ala Ile Pro Ala Ser Val Pro Arg
         -5                  1                   5                  10

Gly Phe Trp Ala Leu Pro Glu Asn Leu Thr Val Val Glu Gly Ala Ser
                    15                  20                  25

Val Glu Leu Arg Cys Gly Val Ser Thr Pro Gly Ser Ala Val Gln Trp
                30                  35                  40

Ala Lys Asp Gly Leu Leu Leu Gly Pro Asp Pro Arg Ile Pro Gly Phe
            45                  50                  55

Pro Arg Tyr Arg Leu Glu Gly Asp Pro Ala Arg Gly Glu Phe His Leu
        60                  65                  70

His Ile Glu Ala Cys Asp Leu Ser Asp Asp Ala Glu Tyr Glu Cys Gln
    75                  80                  85                  90

Val Gly Arg Ser Glu Met Gly Pro Glu Leu Val Ser Pro Arg Val Ile
                95                  100                 105

Leu Ser Ile Leu Val Pro Pro Lys Leu Leu Leu Leu Thr Pro Glu Ala
            110                 115                 120
```

-continued

Gly Thr Met Val Thr Trp Val Ala Gly Gln Glu Tyr Val Val Asn Cys
         125                 130                 135

Val Ser Gly Asp Ala Lys Pro Ala Pro Asp Ile Thr Ile Leu Leu Ser
         140                 145                 150

Gly Gln Thr Ile Ser Asp Ile Ser Ala Asn Val Asn Glu Gly Ser Gln
155                      160                 165                 170

Gln Lys Leu Phe Thr Val Glu Ala Thr Ala Arg Val Thr Pro Arg Ser
                 175                 180                 185

Ser Asp Asn Arg Gln Leu Leu Val Cys Glu Ala Ser Ser Pro Ala Leu
             190                 195                 200

Glu Ala Pro Ile Lys Ala Ser Phe Thr Val Asn Val Leu Phe Pro Pro
         205                 210                 215

Gly Pro Pro Val Ile Glu Trp Pro Gly Leu Asp Glu Gly His Val Arg
         220                 225                 230

Ala Gly Gln Ser Leu Glu Leu Pro Cys Val Ala Arg Gly Gly Asn Pro
235                      240                 245                 250

Leu Ala Thr Leu Gln Trp Leu Lys Asn Gly Gln Pro Val Ser Thr Ala
                 255                 260                 265

Trp Gly Thr Glu His Thr Gln Ala Val Ala Arg Ser Val Leu Val Met
             270                 275                 280

Thr Val Arg Pro Glu Asp His Gly Ala Gln Leu Ser Cys Glu Ala His
         285                 290                 295

Asn Ser Val Ser Ala Gly Thr Gln Glu His Gly Ile Thr Leu Gln Val
         300                 305                 310

Thr Phe Pro Pro Ser Ala Ile Ile Ile Leu Gly Ser Ala Ser Gln Thr
315                      320                 325                 330

Glu Asn Lys Asn Val Thr Leu Ser Cys Val Ser Lys Ser Ser Arg Pro
                 335                 340                 345

Arg Val Leu Leu Arg Trp Trp Leu Gly Trp Arg Gln Leu Leu Pro Met
             350                 355                 360

Glu Glu Thr Val Met Asp Gly Leu His Gly Gly His Ile Ser Met Ser
         365                 370                 375

Asn Leu Thr Phe Leu Ala Arg Arg Glu Asp Asn Gly Leu Thr Leu Thr
         380                 385                 390

Cys Glu Ala Phe Ser Glu Ala Phe Thr Lys Glu Thr Phe Lys Lys Ser
395                      400                 405                 410

Leu Ile Leu Asn Val Lys Tyr Pro Ala Gln Lys Leu Trp Ile Glu Gly
                 415                 420                 425

Pro Pro Glu Gly Gln Lys Leu Arg Ala Gly Thr Arg Val Arg Leu Val
             430                 435                 440

Cys Leu Ala Ile Gly Gly Asn Pro Glu Pro Ser Leu Met Trp Tyr Lys
         445                 450                 455

Asp Ser Arg Thr Val Thr Glu Ser Arg Leu Pro Gln Glu Ser Arg Arg
         460                 465                 470

Val His Leu Gly Ser Val Glu Lys Ser Gly Ser Thr Phe Ser Arg Glu
475                      480                 485                 490

Leu Val Leu Val Thr Gly Pro Ser Asp Asn Gln Ala Lys Phe Thr Cys
                 495                 500                 505

Lys Ala Gly Gln Leu Ser Ala Ser Thr Gln Leu Ala Val Gln Phe Pro
             510                 515                 520

Pro Thr Asn Val Thr Ile Leu Ala Asn Ala Ser Ala Leu Arg Pro Gly
         525                 530                 535

-continued

```
Asp Ala Leu Asn Leu Thr Cys Val Ser Val Ser Ser Asn Pro Pro Val
540                 545                 550
Asn Leu Ser Trp Asp Lys Glu Gly Glu Arg Leu Glu Gly Val Ala Ala
555                 560                 565                 570
Pro Pro Arg Arg Ala Pro Phe Lys Gly Ser Ala Ala Arg Ser Val
            575                 580                 585
Leu Leu Gln Val Ser Ser Arg Asp His Gly Gln Arg Val Thr Cys Arg
            590                 595                 600
Ala His Ser Ala Glu Leu Arg Glu Thr Val Ser Ser Phe Tyr Arg Leu
            605                 610                 615
Asn Val Leu Tyr Arg Pro Glu Phe Leu Gly Glu Gln Val Leu Val Val
    620                 625                 630
Thr Ala Val Glu Gln Gly Glu Ala Leu Leu Pro Val Ser Val Ser Ala
635                 640                 645                 650
Asn Pro Ala Pro Glu Ala Phe Asn Trp Thr Phe Arg Gly Tyr Arg Leu
                655                 660                 665
Ser Pro Ala Gly Gly Pro Arg His Arg Ile Leu Ser Ser Gly Ala Leu
            670                 675                 680
His Leu Trp Asn Val Thr Arg Ala Asp Asp Gly Leu Tyr Gln Leu His
            685                 690                 695
Cys Gln Asn Ser Glu Gly Thr Ala Glu Ala Arg Leu Arg Leu Asp Val
700                 705                 710
His Tyr Ala Pro Thr Ile Arg Ala Leu Gln Asp Pro Thr Glu Val Asn
715                 720                 725                 730
Val Gly Gly Ser Val Asp Ile Val Cys Thr Val Asp Ala Asn Pro Ile
                735                 740                 745
Leu Pro Gly Met Phe Asn Trp Glu Arg Leu Gly Glu Asp Glu Glu Asp
            750                 755                 760
Gln Ser Leu Asp Asp Met Glu Lys Ile Ser Arg Gly Pro Thr Gly Arg
            765                 770                 775
Leu Arg Ile His His Ala Lys Leu Ala Gln Ala Gly Ala Tyr Gln Cys
            780                 785                 790
Ile Val Asp Asn Gly Val Ala Pro Pro Ala Arg Arg Leu Leu Arg Leu
795                 800                 805                 810
Val Val Arg Phe Ala Pro Gln Val Glu His Pro Thr Pro Leu Thr Lys
            815                 820                 825
Val Ala Ala Ala Gly Asp Ser Thr Ser Ser Ala Thr Leu His Cys Arg
            830                 835                 840
Ala Arg Gly Val Pro Asn Ile Val Phe Thr Trp Thr Lys Asn Gly Val
            845                 850                 855
Pro Leu Asp Leu Gln Asp Pro Arg Tyr Thr Glu His Thr Tyr His Gln
860                 865                 870
Gly Gly Val His Ser Ser Leu Leu Thr Ile Ala Asn Val Ser Ala Ala
875                 880                 885                 890
Gln Asp Tyr Ala Leu Phe Thr Cys Thr Ala Thr Asn Ala Leu Gly Ser
            895                 900                 905
Asp Gln Thr Asn Ile Gln Leu Val Ser Ile Ser Arg Pro Asp Pro Pro
            910                 915                 920
Ser Gly Leu Lys Val Val Ser Leu Thr Pro His Ser Val Gly Leu Glu
            925                 930                 935
Trp Lys Pro Gly Phe Asp Gly Gly Leu Pro Gln Arg Phe Cys Ile Arg
940                 945                 950
```

-continued

```
Tyr Glu Ala Leu Gly Thr Pro Gly Phe His Tyr Val Asp Val Val Pro
955                 960                 965                 970

Pro Gln Ala Thr Thr Phe Thr Leu Thr Gly Leu Gln Pro Ser Thr Arg
            975                 980                 985

Tyr Arg Val Trp Leu Leu Ala Ser Asn Ala Leu Gly Asp Ser Gly Leu
            990                 995                 1000

Ala Asp Lys Gly Thr Gln Leu Pro Ile Thr Thr Pro Gly Leu His Gln
            1005                1010                1015

Pro Ser Gly Glu Pro Glu Asp Gln Leu Pro Thr Glu Pro Pro Ser Gly
            1020                1025                1030

Pro Ser Gly Leu Pro Leu Leu Pro Val Leu Phe Ala Leu Gly Gly Leu
1035                1040                1045                1050

Leu Leu Leu Ser Asn Ala Ser Cys Val Gly Gly Val Leu Trp Gln Arg
                1055                1060                1065

Arg Leu Arg Arg Leu Ala Glu Gly Ile Ser Glu Lys Thr Glu Ala Gly
                1070                1075                1080

Ser Glu Glu Asp Arg Val Arg Asn Glu Tyr Glu Glu Ser Gln Trp Thr
            1085                1090                1095

Gly Glu Arg Asp Thr Gln Ser Ser Thr Val Ser Thr Thr Glu Ala Glu
            1100                1105                1110

Pro Tyr Tyr Arg Ser Leu Arg Asp Phe Ser Pro Gln Leu Pro Pro Thr
1115                1120                1125                1130

Gln Glu Glu Val Ser Tyr Ser Arg Gly Phe Thr Gly Glu Asp Glu Asp
                1135                1140                1145

Met Ala Phe Pro Gly His Leu Tyr Asp Glu Val Glu Arg Thr Tyr Pro
            1150                1155                1160

Pro Ser Gly Ala Trp Gly Pro Leu Tyr Asp Glu Val Gln Met Gly Pro
            1165                1170                1175

Trp Asp Leu His Trp Pro Glu Asp Thr Tyr Gln Asp Pro Arg Gly Ile
            1180                1185                1190

Tyr Asp Gln Val Ala Gly Asp Leu Asp Thr Leu Glu Pro Asp Ser Leu
1195                1200                1205                1210

Pro Phe Glu Leu Arg Gly His Leu Val
                1215
```

(2) INFORMATION FOR SEQ ID NO: 3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer exon 2 5'UTR"

(xi) SEQUENCE DESCRIPTION: SEQ ID NO: 3:

GAGAAAGCCA GACAGACGCA G                                       21

(2) INFORMATION FOR SEQ ID NO: 4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear -continued

```
    (ii) MOLECULE TYPE: other nucleic acid
        (A) DESCRIPTION: /desc = "primer intron 2"

(xi) SEQUENCE DESCRIPTION: SEQ ID NO: 4:

AGCTTCCGCT GGTGGCT                                                  17

(2) INFORMATION FOR SEQ ID NO: 5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer intron 23"

(xi) SEQUENCE DESCRIPTION: SEQ ID NO: 5:

CTCGGGGAGA CCCACCC                                                  17

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer intron 26"

(xi) SEQUENCE DESCRIPTION: SEQ ID NO: 6:

CCTGATGCTA ACGGCAGGGC                                               20
```